United States Patent
Jiang et al.

(10) Patent No.: US 9,683,231 B2
(45) Date of Patent: Jun. 20, 2017

(54) RNAI-BASED METHOD OF DRUG SCREENING AND CHARACTERIZATION

(75) Inventors: Hai Jiang, Shanghai (CN); Justin Pritchard, Boston, MA (US); Douglas A. Lauffenburger, Cambridge, MA (US); Michael Hemann, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 412 days.

(21) Appl. No.: 13/993,930

(22) PCT Filed: Dec. 16, 2011

(86) PCT No.: PCT/US2011/065611
§ 371 (c)(1),
(2), (4) Date: Jan. 29, 2014

(87) PCT Pub. No.: WO2012/083231
PCT Pub. Date: Jun. 21, 2012

(65) Prior Publication Data
US 2014/0134635 A1    May 15, 2014

Related U.S. Application Data

(60) Provisional application No. 61/423,975, filed on Dec. 16, 2010.

(51) Int. Cl.
*C12N 15/10* (2006.01)
*C12Q 1/68* (2006.01)
*G01N 33/50* (2006.01)

(52) U.S. Cl.
CPC ....... *C12N 15/1079* (2013.01); *C12Q 1/6883* (2013.01); *C12Q 1/6886* (2013.01); *G01N 33/5023* (2013.01); *C12Q 2600/136* (2013.01); *C12Q 2600/178* (2013.01)

(58) Field of Classification Search
USPC ..... 424/9.1; 435/6.1, 6.11, 91.1, 455, 91.31, 435/6.12, 6.13, 375; 514/44, 1, 2; 536/23.1, 24.5
See application file for complete search history.

(56) References Cited

U.S. PATENT DOCUMENTS

| | | | |
|---|---|---|---|
| 2005/0181385 A1* | 8/2005 | Linsley | C12N 15/111 435/6.16 |
| 2010/0168022 A1* | 7/2010 | Centeno | G01N 33/5073 514/1.1 |
| 2011/0054001 A1 | 3/2011 | Look et al. | |
| 2011/0307427 A1* | 12/2011 | Linke | G01N 33/574 706/12 |
| 2014/0206544 A1 | 7/2014 | Pritchard et al. | |

FOREIGN PATENT DOCUMENTS

WO  WO2012/083231 A9  6/2012
WO  WO2012/083243 A1  6/2012

OTHER PUBLICATIONS

Brummelkamp et al, Nature Chem. Biology, vol. 2, No. 4, pp. 202-206 (2006).*
Jiang et al, Genes & dev., vol. 23, pp. 1895-1909 (2009).*
Mullenders et al, Clin. Cancer Res., vol. 15, No. 18, pp. 5811-5819 (2009).*
Iorns et al, Nature, vol. 6, pp. 556-568 (2007).*
Berns et al, Nature, vol. 428, pp. 431-437 (2004).*
Erker et al (Human Molecular Genetics, vol. 14, No. 12, pp. 1699-1708 (2005).*
Olsson et al (Cell Death and Differentiation, vol. 14, pp. 1561-1575 (2007).*
Chipoy et al, Oncogene, vol. 26, pp. 6653-6664 (2007).*
Adams, J.M., et al., "The C-MYC Oncogene Driven by Immunoglobulin Enhancers Induces Lymphoid Malignancy in Transgenic Mice", *Nature*, 318(6046): 533-538 (1985).
Akhtar, M.S., et al., "TFIIH Kinase Places Bivalent Marks on the Carboxy-Terminal Domain of RNA Polymerase II", *Molecular Cell*, 34: 387-393 (2009).
Bartek, J. and Lucase, J., "Chk 1 and Chk2 Kinases in Checkpoint Control and Cancer", *Cancer Cell*, 3: 421-429 (2003).
Berns, K., et al., "A Large-Scale RNAi Screen in Human Cells Identifies New Components of the p53 Pathway", *Nature*, 428: 431-437 (2004).
Berns, K., et al., "A Large-Scale RNAi Screen in Human Cells Identifies New Components of the p53 Pathway: Supplementary Talbe 1 Genes in the NKI RNAi Library", *Nature*, 428: 7pages (2004).
Blanchard, J.S., "Molecular Mechanisms of Drug Resistance in *Mycobacterium tuberulosis*", Annu. Rev. Biochem., 65: 215-239 (1996).
Bode, A.M. and Dong, Z., "Post-Tranlational Modification of p53 in Tumorigenesis", *Nature Reviews Cancer*, 4: 793-805 (2004).
Borisy, A.A., et al., "Systematic Discovery of Multicomponent Therapeutics", PNAS, 100(13): 7977-7982 (2003).

(Continued)

*Primary Examiner* — Jane Zara
(74) *Attorney, Agent, or Firm* — Hamilton, Brook, Smith & Reynolds, P.C.

(57) ABSTRACT

The invention is directed to a method of characterizing a mechanism of action of an agent (e.g., a chemotherapeutic agent, a genotoxic agent). The method comprises contacting a plurality of populations of cells with an agent to be assessed, wherein each population of cells have one gene of interest targeted by a small hairpin RNA (shRNA) and wherein said gene of interest regulates cell death and a plurality of genes that regulate cell death are targeted in the plurality of populations of cells. A responsiveness of each population of cells to the agent is determined, thereby obtaining an shRNA signature of the agent, so as to identify one or more genes that mediate a response to the agent, thereby characterizing the mechanism of action of the agent. The invention is also directed an article of manufacture for characterizing a mechanism of action of a chemotherapeutic or genotoxic agent.

30 Claims, 24 Drawing Sheets

(56) References Cited

OTHER PUBLICATIONS

Brossier, F., et al., "Detection by GeneType MTBDRsI Test of Complex Mechanisms of Resistance to Second-Line Drugs and Ethambutol in Multidrug-Resistant *Mycobacterium tuberculosis* Complex Isolates", J. Clin. Microbiol. 48(5): 1683-1689 (2010).
Brumbaugh, K.M., et al., "The mRNA Surveillance Protein hSMG-1 Fucntions in Genotoxic Stress Response Pathways in Mammalian Cells", *Molecular Cell*, 14: 585-598 (2004).
Brummelkamp, T., et al., "An shRNA Barcode Screen Provides Insight Into Cancer Cell Vulnerability to MDM2 Inhibitors", Nature Chemical Biology, 2(4): 202-206 (2006).
Budman, D.R., et al., "Dose and Dose Intensity as Determinants of Outcome in the Adjuvant Treatment of Breast Cancer", J. National Cancer Institute, 90(16): 1205-1211 (1998).
Burgess, D.J., et al., "Topoisomerase Levels Determine Chemotherapy Response In Vitro and In Vivo", PNAS, 105(26): 9053-9058 (2008).
Carbone, P.P., et al., "Management of Patients With Malignant Lymphoma" A Comparative Study With Cyclophosphamide and Vinca Alkaloids, Cancer Research, 28(5): 811-822 (1968).
Chen, G., et al., "Prevalence of Multidrug Resistance Related to Activation of the mdr1 Gene in Human Sarcoma Mutants Derived by Single-Step Doxorubicin Selection", Cancer Research 54: 4980-4987 (1994).
Chen, G., et al., "Prevalence of Multidrug Resistance Related to Activation of the mdr1 Gene in Human Sarcoma Mutants Derived by Single-Step Doxorubicin Selection", Chen, G., et al., "MDR1 Activation is the Predominant Resistance Mechanism Selected by Vinblastine in MES-SA Cells", British Journal of Cancer, 83(7): 892-898 (2000).
Cimprich, K.A. and Cortez, D., "ATR: An Essential Regulator of Genome Integrity", *Nature Rev. Mol. Cell Biol.*, 9: 616-627 (2008).
DeVita, V.T. and Schein, P.S., "The Use of Drugs in Combination for the Treatment of Cancer: Rationale and Results", N.Engl. J. Med., 288(19): 998-1006 (1973).
Dickins, R.A., et al., "Probing Tumor Phenotypes Using Stable and Regulated Synthetic microRNA Precursors", Nature Genetics, 37(11): 1289-1295 (2005).
Frei, III, E., "Curative Cancer Chemotherapy", Cancer Research, 45: 6523-6537 (1985).
Frei, III, E., et al., "A Comparative Study of Two Regimens of Combination Chemotherapy in Acute Leukemia", Blood, 13: 1126-1148 (1958).
Frei, III, E., et al., "The Relationship Between High-Dose Treatment and Combination Chemotherapy: The Concept of Summation Dose Intensity", Clin. Cancer Res., 4: 2027-2037 (1998).
Gardner, T.S., et al., "Inferring Genetic Networks and Identifying compound Mode of Action via Expression Profiling", Science, 301: 102-105 (2003).
Giaever, G., et al., "Genomic Profliling of Drug Sensitivities via Induced Haploinsufficiency", Nature Genetics, 21: 278-283 (1999).
Giaever, G., et al., "Chemogenomic Profiling: Identifying the Functional Interactions of Small Molecules in Yeast", PNAS, 101(3): 793-798 (2004).
Goldin, A. and Mantel, N., "The Employment of Combinations of Drugs in the Chemotherapy of Neoplasia: A Review", Cancer Research, 17(7): 635-654 (1957).
Goldin, A., et al., "Factors Influencing Antitumor Synergism: Relation to Screening Methodology", Annals of the NY Acad. of Sciences, 76: 932-938 (1958).
Greco, W.R. et al., "The Search for Cytotoxic Synergy Between Anticancer Agents: A Case of Dorothy and the Ruby Slippers?", J. of the National Cancer Institute, 88(11): 699-700 (1996).
Hieronymus, H., et al., "Gene Expression Signature-Based Chemical Genomic Prediction Identifies a Novel Class of HSP90 Pathway Modulators", Cancer Cell, 10: 321-330 (2006).

Hillenmeyer, M.E., et al., "The Chemical Genomic Portrait of Yeast: Uncovering a Phenotype for All Genes", *Science*, 320: 362-365 (2008).
Hillenmeyer, M.E., et al., "Systematic Analysis of Genome-Wide Fitness DAta in Yeast Reveals Novel Gene Function and Drug Action", *Genome Biology*, 11: R30, 17pages (2010).
Ho, C.H., et al., "A Molecular Barcoded Yeast ORF Library Enables Mode-of-Action Analysis of Bioactive Compounds", Nature Biotechnol., 27(4): 369-377 (2009).
Huel, T., et al., "Distinguishing Rational From Irrational Applications of Pharmacogenetic Synergies From the Bench to Clinical Trials", Cell Cycle, 6(11): 1336-1341 (2007).
Hughes, T.R., et al., "Functinal Discovery via a Compendium of Expression Profiles", Cell, 102: 109-126 (2000).
Iorns, E., et al., "Utilizing RNA Interference to Enhance Cancer Drug Discovery", Nature Reviews Drug Discovery, 6: S56-S68 (2007).
Jiang, H., et al., "The Combined Status of ATM and p53 Link Tumor Development With Therapeutic Response", Genes & Development, 23: 1895-1909 (2009).
Jiang H., et al., "A Mammalian Functional-Genetic Approach to Characterizing Cancer Therapeutics", Nat. Chem. Biol., 7(2): 92-100 (2011).
Krutzik, P.O., et al., "High-Content Single-Cell Drug Screening With Phosphospecific Flow Cytometry", Nat. Chem. Biol., 4(2): 132-142 (2008).
Lamb, J., et al., "The Connectivity Map: Using Gene-Expression Signatures to Connect Small Molecules, Genes, and Disease", Science, 313: 1929-1935 (2006).
Lau, D.H.M., et al., "Multifactorial Mechanisms Associated With Broad Cross-Resistance of Ovarian Carcinoma Cells Selected by Cyanomorpholino Doxorubicin", Cancer Research, 51: 5181-5187 (1991).
Lavin, M.F., "Ataxia-Telangiectasia: From a Rare Disorder to a Paradigm for Cell Signalling and Cancer", Nature Reviews Molecular Cell Biology, 9: 759-769 (2008).
Law, L.W., "Effects of Combinations of Antileukemic Agents on an Acute Lymphocytic Leukemia of Mice", Cancer Research, 12: 871-878 (1952).
Law, L.W., "Origin of the Resistance of Leukaemic Cells to Folic Acid Antagonists", Nature, 169: 628-629 (1952).
Lehár, J., et al., "Synergistic Drug Combinations Tend to Improve Therapeutically Relevant Selectivity", Nature Biotechnol., 27: 659-666 (2009).
Lindemann, R.K., et al., "Analysis of the Apoptotic and Therapeutic Activities of Histone Deacetylase Inhibitors by Using a Mouse Model of B Cell Lymphoma", PNAS, 104(19): 8071-8076 (2007).
Ljungman, M. and Paulsen, M.T., "The Cyclin-Dependent Kinase Inhibitor Roscovitine Inhibits RNA Synthesis and Triggers Nuclear Accumulation of p53 That is Unmodified at Ser15 and Lys382", Molecular Pharmacology, 60(4): 785-789 (2001).
Longley, D.B., et al., "5-Fluorouracil: Mechanisms of Action and Clinical Strategies", Nat. Rev. Cancer, 3(5): 330-338 (2003).
Lowe, S.W., et al., "p53-Dependent Apoptosis Modulates the Cytotoxicity of Anticancer Agents", Cell, 74(6): 957-967 (1993).
Lowe, S.W., et al., "p53 Status and the Efficacy of Cancer Therapy In Vivo", Science, 266: 807-810 (1994).
Lu, C. and El-Deiry, W.S., "Targeting p53 for Enhanced Radio- and Chemo-Sensitivity", *Apoptosis*, 14(4): 597-606 (2009).
Lum, P.Y., et al., "Discovering Modes of Action for Therapeutic Compounds Using a Genome-Wide Screen of Yeast Heterozygotes", Cell, 116: 121-137 (2004).
Luria, S.E. and Delbrück, M., "Mutations of Bacteria From Virus Sensitivity to Virus Resistance", Genetics, 28: 491-511 (1943).
MacCallum, D.E., et al., "Seliciclib (CYC202, R-Roscovitine) Induces Cell Death in Multiple Myeloma Cells by Inhibition of RNA Polymerase II-Dependent Transcription and Down-Regulation of McI-1", Cancer Resarch, 65(12): 5399-5407 (2005).
Mojas, N., et al., "Mismatch Repair-Dependent Processing of Methylation Damage Gives Rise to Persistent Single-Stranded Gaps in Newly Replicated DNA", *Genes Dev.*, 21: 3342-3355 (2007).

(56) References Cited

OTHER PUBLICATIONS

Mullenders, J., et al., "Candidate Biomarkers of Response to an Experimental Cancer Drug Identified Through a Large-Scale RNA Interference Genetic Screen", *Clinical Cancer Research*, 15(18): 5811-5819 (2009).
Mullighan, C.G., et al., "Genomic Analysis of the Clonal Origins of Relapsed Acute Lyphoblastic Leukemia", Science, 322: 1377-1380 (2008).
Newcombe, H.B. and Nyholm, M.H., "The Inheritance of Streptomycin Resistance and Dependence in Crosses of *Escherichia coli*", Genetics, 35: 603-611 (1950).
Parsons, A.B., et al., "Integration of Chemical-Genetic and Genetic Interaction Data Links Bioactive Compounds to Cellular Target Pathways", *Nature Biotechnology*, 22(1): 62-69 (2004).
Parsons, A.B., et al., "Exploring the Mode-of-Action of Bioactive Compounds by Chemical-Genetic Profiling in Yeast", *Cell*, 126: 611-625 (2006).
Pearce, A.K. and Humphrey, T.C., "Integrating Stress-Response and Cell-Cycle Checkpoint Pathways", *Trends in Cell Biology*, 11(10): 426-433 (2001).
Perlman, Z.E., et al., "Multidimensional Drug Profiling by Automated Microscopy", Science, 306: 1194-1198 (2004).
Pritchard, J.R., et al., "Thre-Kinase Inhibitor Combination Recreates Multipathway Effects of a Geldanamycin Analogue on Hepatocellular Carcinoma Cell Death", *Mol Cancer Ther*, 8: 2183-2192 (2009).
Ramalingam, S.S., et al., "A Phase I Study of 17-Allylamino-17-Demethoxygeldanainycin Combined With Paclitaxel in Patients With Advanced Solid Malignancies", Clin. Cancer Res., 14(11): 3456-3461 (2008).
Reinhardt, H.C., et al., "p53-Deficient Cells Rely on ATM-andATR-Mediated Checkpoint Signaling Through the p38MAPK/MK2 Pathway for Survival After DNA Damage", Cancer Cell, 11: 175-189 (2007).
Rihel, J., et al., "Zebrafish Behavioral Profiling Links Drugs to Biological Targets and Rest/Wake Regulation", Science, 327: 348-351 (2010).
Sato, S., et al., "Biochemical Target Isolation for Novices: Affinity-Based Strategies", *Chemistry & Biology*, 17: 616-623 (2010).
Schmitt, C.A., et al., "INK4a/ARF Mutations Accelerate Lymphomagenesis and Promote Chemoresistance by Disabling p53", *Genes & Development*, 13: 2670-2677 (1999).
Shoemaker, R.H., "The NCI60 Human Tumour Cell Line Anticancer Drug Screen", *Nature Review Cancer*, 6: 813-823 (2006).
Skipper, H.E., et al., Experimental Evaluation of Potential Anticancer Agents. Cancer Chemotherapy Reports Part I, 35: 1-111 (1964).
Suzuki R. and Shimodaira, H., "Pvclust: An R Package for Assessing the Uncertainty in Hierarchical Clustering", *Bioinformatics*, 22(12): 1540-1542 (2006).
Swann, P.F., et al., "Role of Postreplicative DNA Mismatch Repair in the Cytotoxic Action of Thioguanine", *Science*, 273: 1109-1111 (1996).
Telenti, A., et al., "Detection of Rifampican-Resistance Mutations in *Mycobacterium tuberculosis*", Lancet, 341(8846): 647-650 (1993).

Weinstein, J.N., et al., "An Information-Intensive Approach to the Molecular Pharmacology of Cancer", Science, 275: 343-349 (1997).
Whitehurst, A.W., et al., "Synthetic Lethal Screen Identification of Chemosensitizer Loci in Cancer Cells", *Nature*, 446: 815-819 (2007).
Williams, R.T., et al., "Arf Gene Loss Enhances Oncogenicity and Limits Imatinib Response in Mouse Models of Bcr-Abl-Induced Acute Lymphoblastic Leukemia", *PNAS*, 103(17): 6688-6693 (2006).
Youle, R. J. and Strasser, A., "The BCL-2 Protein Family: Opposing Activities That Mediate Cell Death", Nature Reviews Molecular Cell Biology, 9: 47-59 (2008).
Notification of Transmittal of the International Search Report and the Written Opinion of the International Searching Authority for PCT/US2011/065611, "RNAi-Based Method of Drug Screening and Characterization"; date of mailing May 30, 2012.
Notification of Transmittal of the International Search Report and the Written Opinion of the International Searching Authority for PCT/US2011/065630, "RNAi-Based Method of Drug Screening and Characterization"; date of mailing May 23, 2012.
International Preliminary Report on Patentability for PCT/US2011/065611, RNAi-Based Method of Drug Screening and Characterization; date of issuance Jun. 18, 2013.
International Preliminary Report on Patentability for PCT/US2011/065630, RNAi-Based Method of Drug Screening and Characterization; date of issuance Jun. 18, 2013.
Paddison, P.J., et al., "Short Hairpin RNAs (shRNAs) Induce Sequence-Specific Silencing in Mammalian Cells", Genes & Development, 16: 948-958 (2002).
Non-Final Office Action for U.S. Appl. No. 13/99994,057, "RNAi-Based Method of Screening and Characterizing Drug Combinations", date of mailing Dec. 1, 2015.
Assinder, S.J., et al., "The TGF-β, PI3K/Akt and PTEN Pathways: Established and Proposed Biobhemical Integrations in Prostate Cancer", *Biochem. J.*, 417:411-421 (2009).
Awuah, S.G., et al., "A Platinum(IV) Pro-Drug Preferentially Targets IDO Providing Enhanced Ovarian Cancer Immuno-Chemotherapy", *J Am Chem Soc.*, 137(47):14854-14857 (2015).
Non-Final Office Action for U.S. Appl. No. 13/994,057, "RNAi-Based Method of Drug Screening and Characterization Drug Combinations," mailed Jun. 23, 2016.
Pritchard, J.R., et al., "Defining Principles of Combination Drug Mechanisms of Action", *PNAS*, E170-E179 (2012).
Suntharalingam, K., et al., "Bidentate Ligands on Osmium(VI) Nitrido Complexes Control Intracellular Targeting and Cell Death Pathways", *J Am Chem Soc.*, 135(38):14060-14063 (2013).
Suntharalingam, K., et al., "A Breast Cancer Stem Cell-Selective, Mammospheres-Potent Osmium(VI) Nitrido Complex", *J Am Chem Soc*, 136:14413-14416 (2014).
Suntharalingam, K., et al., "Necroptosis-Inducing Rhenium(V) Oxo Complexes", *J Am Chem Soc*, 137(8):2967-2974 (2015).
Zhao, B., et al., "Addressing Genetic Tumor Heterogeneity Through Computationally Predictive Combination Therapy", *Cancer Discov.*, 4(2): 166-174 (2014).
Notice of Allowance for U.S. Appl. No. 13/994,057, Date Mailed: Feb. 2, 2017.

\* cited by examiner

1c

1d

Figures 2a and 2b
2a
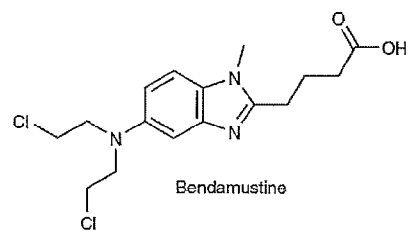
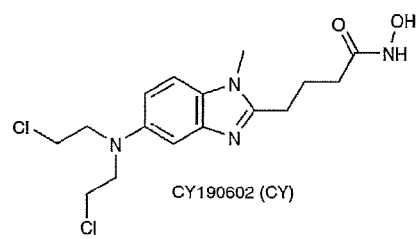
2b
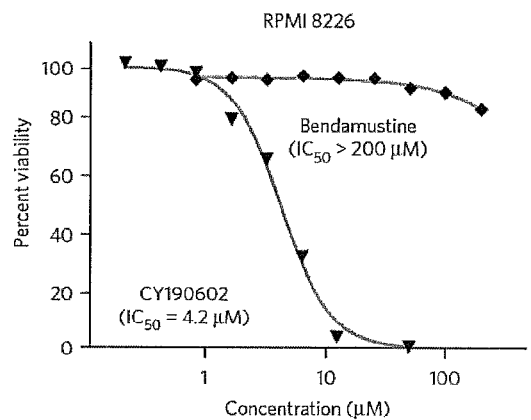
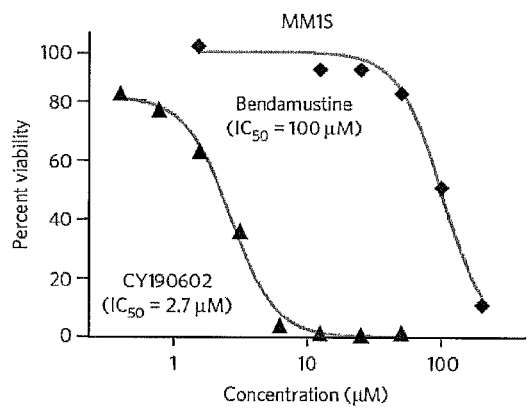

3d

3e

4a

4b

5a Initial category definition from training set

Test compound

Compound is within the reference cluster

Compound expands the cluster definition

5b Calculate drug category pairwise distances

Training set with drug categories

5c Distribution of cluster sizes for false prediction expansion

RNAI-BASED METHOD OF DRUG SCREENING AND CHARACTERIZATION

RELATED APPLICATION(S)

This application is the U.S. National Stage of International Application No. PCT/US2011/065611, filed Dec. 16, 2011, which designates the U.S., published in English, and claims the benefit of U.S. Provisional Application No. 61/423,975, filed on Dec. 16, 2010.

The entire teachings of the above applications are incorporated herein by reference.

GOVERNMENT SUPPORT

This invention was made with government support under Grant Nos. R01 CA128803 and U54 CA112967 awarded by the National Institutes of Health. The government has certain rights in this invention.

BACKGROUND OF THE INVENTION

Chemotherapy remains the frontline therapy for systemic malignancies. However, drug development has been severely hampered by an inability to efficiently elucidate mechanisms of drug action. This limits both the development of modified compounds with improved efficacy and the capability to predict mechanisms of drug resistance and select optimal patient populations for a given agent. Although drug-target interactions have traditionally been examined using biochemical approaches (Sato, S., et al., Chem. Biol. 17, 616-623 (2010)), a number of genetic strategies have been developed to identify pathways targeted by uncharacterized small molecules. A well-established genetic approach to drug classification is chemogenomic profiling in yeast (Giaever, G, et al. Nat. Genet, 21, 278-283 (1999); Giaever, G, et al. Proc, Natl. Acad, Sci. USA 101, 793-798 (2004); Lum, P. Y. et al, Cell 116, 121-137 (2004); Parsons, A, B, et al. Nat. Bioteehnol. 22, 62-69 (2004); Hillenmeyer, M. E. et al. Science 320, 362-365 (2008)). In this approach, bar-coded yeast deletion strains are exposed to select agents, and genotype-dependent drug sensitivity is used to identify genes and pathways affected by a given drug, as well as to develop a response signature that can be compared with other chemical or genetic perturbations (Parsons, A, B, et al. Nat. Bioteehnol. 22, 62-69 (2004); Parsons, A. B. et al. Cell 126, 611-625 (2006); Hillenmeyer, M. E. et al. Genome Biol. 11, R30 (2010)). This approach has proven quite powerful and has been broadly disseminated; however, its efficacy in interrogating cancer chemotherapeutics is limited by the lack of conservation of certain drug targets from yeast to mammals. This is a particular problem in the context of targeted therapeutics, which are frequently directed toward alterations that are specific to mammalian tumors.

More recently, genetic approaches have been developed to examine drug action in mammalian settings. One such approach is to examine drug response in a diverse panel of tumor cell lines (Shoemaller, R. H. Nat. Rev. Cancer 6, 813-823 (2006)). In this case, the pattern of cell line sensitivity and resistance can serve as a signature that defines drug mechanism. Additionally, drug response can be correlated with the presence of specific cancer related alterations, although this analysis can be confounded by the large diversity of alterations present in a given tumor. An alternative approach is to compare the global transcriptional changes induced by test compounds to those induced by known drugs or defined genetic alterations (Hughes. T. R. et al. Cell 102, 109-126 (2000); Gardner, T. S et al., Science 301, 102-105 (2003); Lamb, I. et al. Science 313, 1929-1935 (2006); Hieronymus, H. et al. Cancer Cell, 10, 321-330 (2006)). Gene expression changes are used as signatures that are characteristic of exposure to a given agent or the presence of a specific cellular state, and common expression changes can be used to cluster similar small molecules. Although each of these approaches have yielded important new insights into drug action, these strategies retain a level of technical variability and resource requirement that limits both disseminated use and overall efficacy.

Thus, a need exists for improved methods that screen and characterize drugs.

SUMMARY OF THE INVENTION

Described herein is a tractable ribonucleic acid interference-based (RNAi-based) approach that represents a simple yet powerful platform for drug screening and characterization.

Specifically, the invention is directed to a method of characterizing a mechanism of action of an agent (e.g., a chemotherapeutic agent, a genotoxic agent). The method comprises contacting a plurality of populations of cells with an agent to be assessed, wherein each population of cells have one gene of interest targeted by a small hairpin RNA (shRNA) and wherein said gene of interest regulates cell death and a plurality of genes that regulate cell death are targeted in the plurality of populations of cells. A responsiveness of each population of cells to the agent is determined, thereby obtaining an shRNA signature of the agent, so as to identify one or more genes that mediate a response to the agent, thereby characterizing the mechanism of action of the agent.

In another aspect, the invention is directed an article of manufacture for characterizing a mechanism of action of a chemotherapeutic or genotoxic agent. In one aspect, the article of manufacture comprises a plurality of populations of cells, each population having an shRNA that targets a gene of interest that mediates a response to a chemotherapeutic or genotoxic agent, and an algorithm for clustering plurality of chemotherapeutic or genotoxic agents into one or more groups based on a responsiveness of each population of cells to each agent. In particular aspect, the ATM, Chk2 and p53 genes are targeted. In other aspects, the p53, ATR, Chk1, Chk2, Smg-1, DNA-PKcs, Bok and Bim genes are targeted.

BRIEF DESCRIPTION OF THE DRAWINGS

FIGS. 2a-2d: RNAi-based characterization of a compound derivative of bendamustine. (2a) The chemical structures of bendamustine and a chemical derivative, CY190602. (2b) Dose response curves comparing the viability of the multiple myeloma cell lines RPMI-8226 (top) and MM1S (bottom) following treatment with bendamustine or CY190602. (2c) RI patterns for bendamustine, CY190602 and a related compound, chlorambucil (CBL). Bendamustine and CY190602 were used at LD80-90 of 110 μM and 1.4 respectively. (2d) The branching pattern for the 18 reference drugs plus bendamustine and CY190602.

DETAILED DESCRIPTION OF THE INVENTION

Figure 1A:
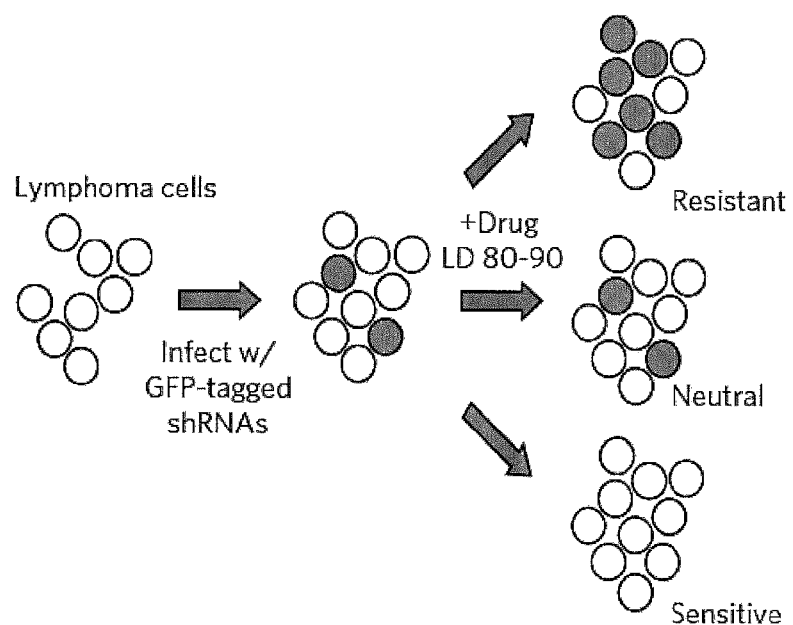
FIGS. 1a-1d: Functional characterization of chemotherapeutic drugs according to patterns of shRNA-conferred drug resistance or sensitivity. (1a) A diagram showing the principle of GFP-based competition assays. Suppression of genes that alter drug sensitivity leads to changes in the percentage of GFP-positive cells after treatment, which can be used to calculate the R1 (see Methods). (1b) Unsupervised clustering of RI values of 15 reference compounds. Agglomerative hierarchical clustering was performed on log-transformed RI values for the initial 15 reference drugs, using a correlation metric and centroid linkage. Bootstrapping data is shown to indicate clustering robustness. 'Approximately unbiased' (AU) values from the PVclust function are indicated next to the relevant branches in the clustergram. (1c) The branching pattern for SAHA, DAC and Rosco and the 15 reference chemodrugs. Numbers below the dendogram demarcate drug categories. (1d) A heat map showing the response of cells expressing shRNAs targeting the Bim transcriptional regulator Chop and Foxo3a to SAHA and DAC. Log-transformed R1 values are shown.

A description of example embodiments of the invention follows.

Identifying mechanisms of drug action remains a fundamental impediment to the development and effective use of chemotherapeutics. An RNA interference (RNAi)-based strategy to characterize small-molecule function in mammalian cells is described herein. By examining the response of cells expressing short hairpin RNAs (shRNAs) to a diverse selection of chemotherapeutics, a functional shRNA signature that accurately grouped drugs into established biochemical modes of action was generated. This, in turn, provided a diversely sampled reference set for high-resolution prediction of mechanisms of action for poorly characterized small molecules. The predictive shRNA target set was further reduced to as few as eight genes and, using a newly derived probability-based nearest-neighbors approach, the predictive power of this shRNA set was extended to characterize additional drug categories. Thus, the focused shRNA phenotypic signature described herein provided a highly sensitive and tractable approach for characterizing new anticancer drugs (see Jiang, H., et al., Nature Chemical Biology 7, 92-100 (2011) which is incorporated herein by reference).

Accordingly, the invention is directed to a method of characterizing a mechanism of action of an agent. The method comprises contacting a plurality of populations of cells with an agent to be assessed, wherein each population of cells have one gene of interest targeted by a small hairpin RNA (shRNA) and wherein said gene of interest regulates cell death and a plurality of genes that regulate cell death are targeted in the plurality of populations of cells. A responsiveness of each population of cells to the agent is determined, thereby obtaining an shRNA signature of the agent, so as to identify one or more genes that mediate a response to the agent, thereby characterizing the mechanism of action of the agent.

As will be appreciated by those of skill in the art, the mechanism of action of a variety of agents can be characterized using the methods described herein. For example, the agent can be a chemical compound, a nucleic acid, a peptide (a protein), a lipid, a sugar (e.g., polysaccharide), a lipopolysaccharide and the like. In one aspect, the agent is a chemotherapeutic agent. In another aspect, the agent is a genotoxic agent. In yet other aspects, the agent is a derivative of a chemotherapeutic or genotoxic agent.

There are a variety of mechanisms of action by which agents (e.g., chemotherapeutic agents) exert their effects. Examples of mechanisms of action of a chemotherapeutic agent include inhibition of a topoisomerase, cross linking of DNA, inducement of single stand break of DNA, inhibition of nucleic acid synthesis, inhibition of mitosis, inhibition of RNA transcription, inhibition of histone modification enzymes, inhibition of heat shock proteins (e.g., Hsp90), alkylation of DNA, inhibition of proteasomes inducement of apoptosis or the like. The methods described herein can further comprise classifying the agent within a group of agents having in common one or more mechanisms of action.

As described herein, the method of determining a mechanism of action of an agent involves contacting a plurality of populations of cells with an agent to be assessed wherein each population of cells has one gene of interest that is not functional (e.g., not expressed). In a particular aspect, the method of determining a mechanism of action of an agent involves contacting a plurality of populations of cells with an agent to be assessed wherein each population of cells have one gene of interest targeted by a small hairpin (shRNA). As is known in the art, shRNA is a ribonucleic acid (RNA) polymer that is designed based on the study of naturally-occurring hairpin RNAs involved in RNA interference (RNAi). shRNA function in the cell is to drive the degradation of messenger RNAs (mRNAs) in a sequence-specific manner. More specifically, shRNA is a short sequence of RNA which makes a tight hairpin turn and can be used to silence gene expression via RNA interference (e.g., Paddison, P., et al., Genes Dev. 16 (8): 948-958 (2002)). That is, in one aspect of the method described herein, each shRNA acts to knock down one gene.

In particular aspects, the method comprises introducing the plurality of shRNAs targeting the plurality of genes of interest into the plurality of populations of cells, wherein each shRNA targets one gene of interest that regulates cell death, wherein each population of cells have one gene of interest targeted. In other aspects, the method can comprise introducing the plurality of shRNAs which suppresses expression of the plurality of genes into the plurality of cells, wherein each shRNA suppresses expression of one gene that regulates cell death, and one gene is suppressed in each cell.

As will be appreciated by those of skill in the art there are a number of genes that regulate cell death. In a particular aspect, the gene that regulates cell death is a gene in the Bcl2 family of genes, a p53 gene, or a p53-activating kinase gene. Examples of a gene in the Bcl2 family of genes includes a Bax gene, Bak gene, a Bok gene, a Bim gene, a Bid gene, a Puma gene, a Noxa gene, a Bad gene, a Bmf gene, a Bik gene, a Hrk gene, a Bclx gene, a Bab gene, a Bclw gene, an A1 gene, a Bclg gene, a Mill gene, a Mule gene, a BPR gene, a BNIP gene, a Bad gene, a Bcl2 gene, or a Mcl 1 gene. Examples of a p53 activating kinase gene include an ATM gene, an ATR gene, a Chk1 gene, a Chk2 gene, a DNAPKcs gene, a Smg-1 gene, a JNK1 gene or a p38 gene.

In the methods of the invention a plurality of genes that regulate cell death are targeted in the plurality of cell populations. In particular aspects, three genes, four genes, five genes, six genes, seven genes, eight genes, nine genes, ten genes, eleven genes, twelve genes, thirteen genes, fourteen genes, fifteen genes, sixteen genes, seventeen genes, eighteen genes, nineteen genes, twenty genes, twenty one genes, twenty two genes, twenty three genes, twenty four genes, twenty five genes, twenty six genes, twenty seven genes, twenty eight genes, twenty nine genes, thirty genes or more are targeted by the corresponding shRNAs. As will be appreciated by those of skill in the art, libraries encompassing hundreds and thousands of such genes can be used in the methods described herein.

The particular genes chosen for targeting can thereby provide a particular shRNA signature of the agent when assessed using the methods provided herein. For example, in a particular aspect, the plurality of genes targeted by the corresponding shRNAs are ATM, Chk2 and p53 genes, thereby allowing one to characterize the mechanism of action of an agent as a shATM-Chk2-p53 'resistance signature'. In another aspect, the plurality of genes targeted by the corresponding shRNAs are p53, ATR, Chk1, Chk2, Smg-1, DNA-PKcs, Bok and Bim genes, thereby allowing one to characterize the mechanism of action of an agent as a shp53, ATR, Chk1, Chk2, Smg-1, DNA-PKcs, Bok, Bim 'resistance signature'. As will be appreciated by those of skill in the art, other resistant signatures can be determined as described herein.

In the methods of the invention, the shRNAs can be introduced into the cells using a variety of methods. For example, as described herein a viral vector is used. Numerous viral vectors that can be used in the methods are known to those of skill in the art. Specific examples include a retroviral vector, an adenoviral vector and the like.

As will be appreciated by those of skill in the art, the vector can include other components. In a particular aspect, the viral vector further expresses a marker gene. Any variety of marker genes can be incorporated into the viral vector. In one aspect, the marker gene is a fluorescent marker gene. In a particular aspect, the marker gene is green fluorescent protein (GFP) gene.

Marker genes and the expression thereof can be measured in the cell populations using a variety of techniques known in the art. Thus, the methods described herein can further comprise measuring the marker gene (e.g., a fluorescent marker gene or GFP gene) expression level in each population of cells. In one aspect, flow cytometry is used to measure the marker gene or expression thereof.

As described herein a responsiveness of each population of cells to the agent is determined, thereby obtaining the shRNA signature of the agent so as to identify one or more genes that mediate a response to the agent. Examples of a type of responsiveness that can be determined include resistance or sensitivity to the agent. In one aspect, the responsiveness of each population of cells to the agent is a relative level of chemo-resistance and sensitization conferred by each shRNA. In a particular aspect, the responsiveness is a relative survival rate of each population of cells compared to control cells that do not contain said shRNA targeting the gene of interest.

The determination of responsiveness can be determined using a variety of methods. In one aspect, the determination of the responsiveness is accomplished using cell flow cytometry, hybridization techniques or sequencing techniques.

In the methods of the invention the plurality of populations of cells can be contacted with the chemotherapeutic agent for any suitable amount of time. In some aspects, the plurality of populations of cells are contacted once with the agent. In other aspects, the plurality of populations of cells are contacted repeatedly (more than once) with the agent. In addition, the plurality of populations of cells can be contacted with the agent for about 1 hour, 4 hours, 8 hours, 12 hours, 16 hours, 20 hours, 24 hours, 28 hours, 32 hours, 36 hours, 40 hours, 44 hours, 48 hours, 52 hours, 56 hours, 60 hours, 64 hours, 68 hours, 72 hours, 76 hours, 80 hours, 84 hours, 88 hours, 92 hours, 96 hours, 100 hours or longer.

In the methods described herein, the amount of agent that is contacted with the plurality of populations of cells will vary and will deoend on a variety of factors (e.g., the type of agent being assessed; the type of response being sought, etc). For example, the amount (e.g., concentration) of agent that is contacted with the populations of cells can be based on an agent's lethal dose (LD), if known. The LD of the agent that can be used in the methods includes the lethal dose that is sufficient to kill 50% of a cell population (LD50), 60% of a cell population (LD60), 70% of a cell population (LD70), 80% of a cell population (LD80), 90% of a cell population (LD90), or 100% of a cell population (LD100). In particular aspects, the agent is used in an effective amount to induce a response in cells that do not contain said shRNA targeting said gene of interest.

Any of a variety of cells can be used in the methods of the invention. In one aspect, the cells are mammalian cells. Examples of mammalian cells include primate cells (e.g., human cells), murine cells (e.g., mouse cells, rat cells), feline cells, canine cells, bovine cells and the like. In a particular aspect, the cells are from a pathological or diseased source. For example, the cells can be tumor cells. Examples of tumor cells include lymphoma cells, acute lymphocytic leukemia cells and the like.

As will be appreciated by those of skill in the art, the methods described herein can further comprise comparing the responsiveness of each population of cells to the agent to a control. As will be apparent to those of skill in the art, a variety of suitable controls can be used. In one aspect, the control is a population of cells into which the shRNA targeting the gene of interest has not been introduced.

As will also be appreciated by those of skill in the art, the methods of the invention can be performed in vitro, as described herein. Alternatively, or additionally, the methods described herein can be performed in vivo. An example of an in vivo method involves the use of a pooled shRNA format. In this aspect, shRNAs are pooled and transduced into a target cell population and the population is then engrafted into a recipient non-human mammal such as a rodent (e.g., a mouse or a rat). A pretreatment baseline is established by sequencing or hybridization. The non-human mammals are dosed with drugs and following treatment, reassessed for the shRNA pool composition.

As shown herein, the methods of the invention can also be automated. In one aspect, the methods can further comprise using an algorithm to cluster a plurality of agents into groups based on the responsiveness of each population of cells to each agent.

Figure 15:
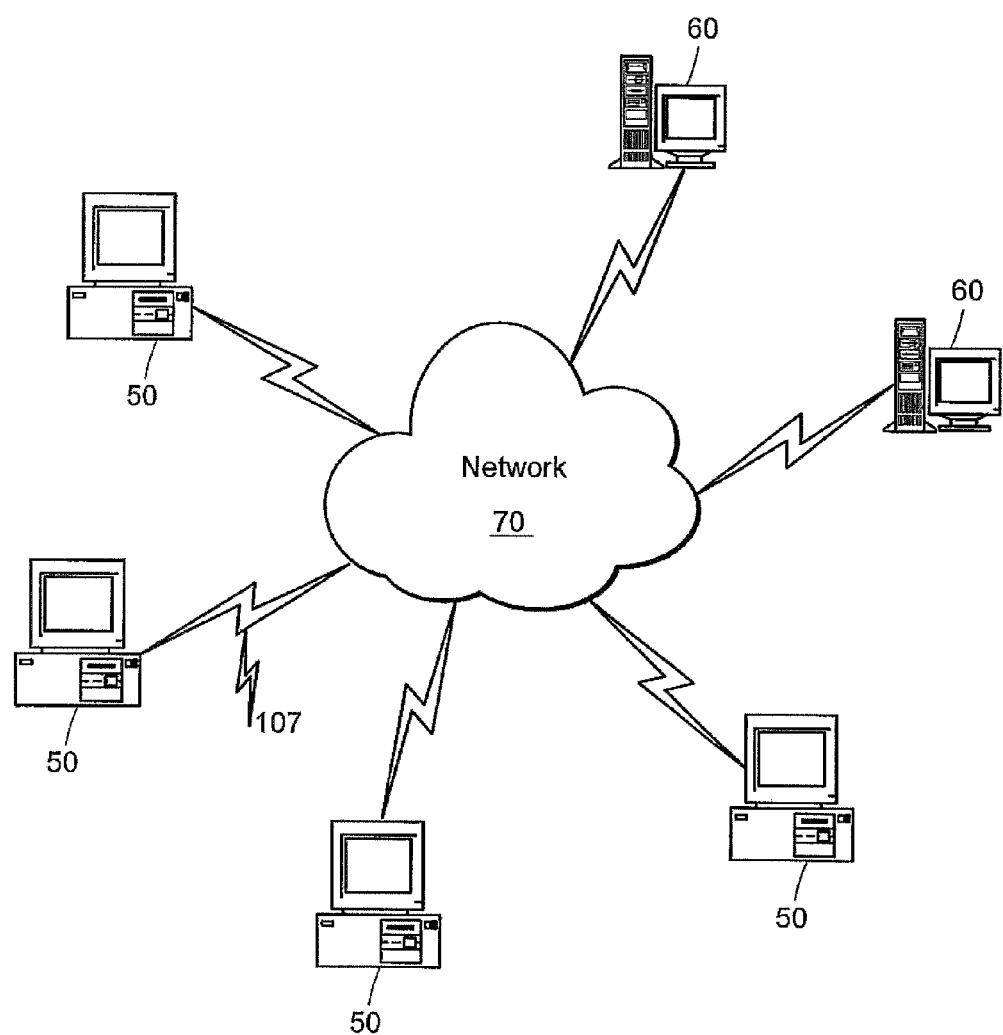
FIG. 15: Illustration of a computer network or similar digital processing environment in which the present invention may be implemented.

FIG. 15 illustrates a computer network or similar digital processing environment in which the present invention may be implemented. For example, a computer(s)/devices 50 and server computer(s) 60 provide processing, storage, and input/output devices executing application programs and the like. The computer(s)/devices 50 can also be linked through communications network 70 to other computing devices, including other client devices/processes 50 and server computer(s) 60. A communications network 70 can be part of a remote access network, a global network (e.g., the Internet), a worldwide collection of computers, Local area or Wide area networks, and gateways that currently use respective protocols (TCP/IP, Bluetooth, etc.) to communicate with one another. Other electronic device/computer network architectures are suitable.

Figure 16:
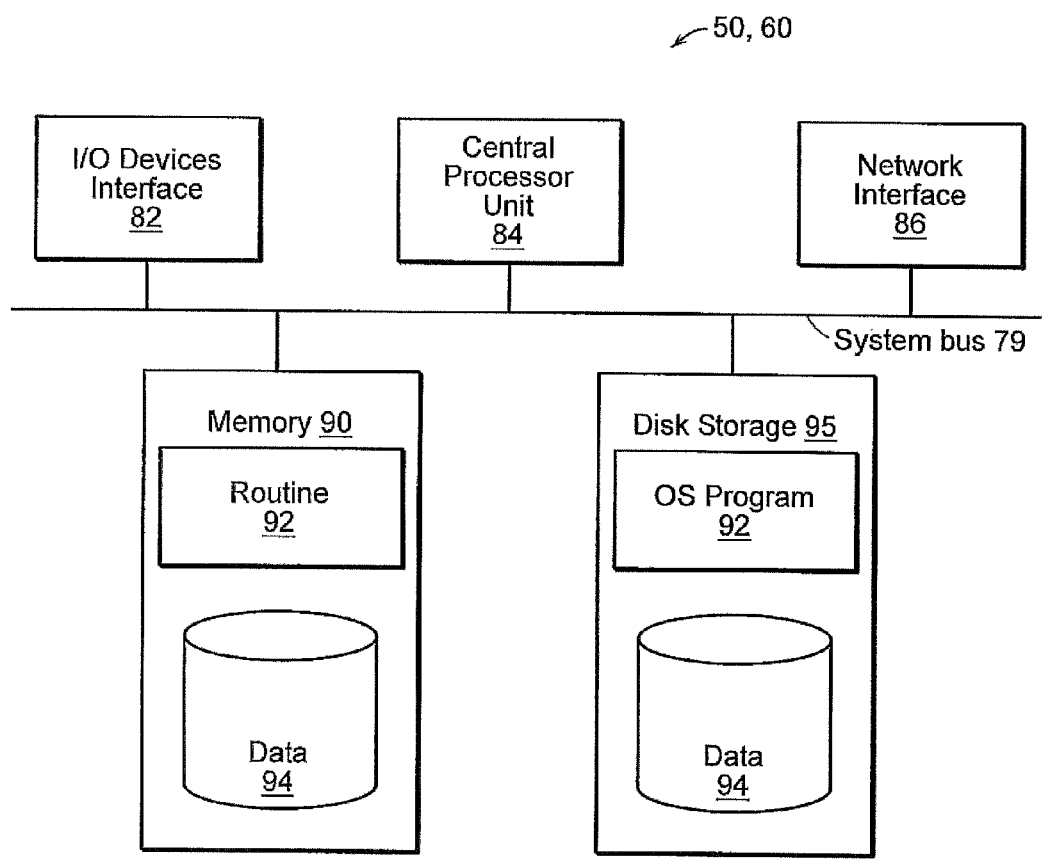
FIG. 16: Diagram of the internal structure of a computer (e.g., client processor/device 50 or server computers 60) in the computer system of FIG. 15.

FIG. 16 is a diagram of the internal structure of a computer (e.g., processor/device 50 or server computers 60) in the computer system of FIG. 15. Each computer 50, 60 contains system bus 79, where a bus is a set of hardware lines used for data transfer among the components of a computer or processing system. Bus 79 is essentially a shared conduit that connects different elements of a computer system (e.g., processor, disk storage, memory, input/output ports, network ports, etc.) that enables the transfer of information between the elements. Attached to system bus 79 is I/O device interface 82 for connecting various input and output devices (e.g., keyboard, mouse, displays, printers, speakers, etc.) to the computer 50, 60. Network interface 86 allows the computer to connect to various other devices attached to a network (e.g., network 70 of FIG. 4). Memory 90 provides volatile storage for computer software instructions 92 and data 94 used to implement an embodiment of the present invention. Disk storage 95 provides non-volatile storage for computer software instructions 92 and data 94 used to implement an embodiment of the present invention. Central processor unit 84 is also attached to system bus 79 and provides for the execution of computer instructions.

In one embodiment, the processor routines 92 and data 94 are a computer program product (generally referenced 92), including a computer readable medium (e.g., a removable storage medium such as one or more DVD-ROM's, CD-ROM's, diskettes, tapes, etc.) that provides at least a portion of the software instructions for the invention system. Computer program product 92 can be installed by any suitable software installation procedure, as is well known in the art. In another embodiment, at least a portion of the software instructions may also be downloaded over a cable, communication and/or wireless connection. In other embodiments, the invention programs are a computer program propagated signal product 107 embodied on a propagated signal on a propagation medium (e.g., a radio wave, an infrared wave, a laser wave, a sound wave, or an electrical wave propagated over a global network such as the Internet, or other network(s)). Such carrier medium or signals provide at least a portion of the software instructions for the present invention routines/program 92.

In alternate embodiments, the propagated signal is an analog carrier wave or digital signal carried on the propagated medium. For example, the propagated signal may be a digitized signal propagated over a global network (e.g., the Internet), a telecommunications network, or other network. In one embodiment, the propagated signal is a signal that is transmitted over the propagation medium over a period of time, such as the instructions for a software application sent in packets over a network over a period of milliseconds, seconds, minutes, or longer. In another embodiment, the computer readable medium of computer program product 92 is a propagation medium that the computer system 50 may receive and read, such as by receiving the propagation medium and identifying a propagated signal embodied in the propagation medium, as described above for computer program propagated signal product.

Generally speaking, the term "carrier medium" or transient carrier encompasses the foregoing transient signals, propagated signals, propagated medium, storage medium and the like.

The invention is also directed an article of manufacture for characterizing a mechanism of action of a chemotherapeutic or genotoxic agent. In one aspect, the article of manufacture comprises a plurality of populations of cells, each population having an shRNA that targets a gene of interest that mediates a response to a chemotherapeutic or genotoxic agent, and an algorithm for clustering plurality of chemotherapeutic or genotoxic agents into one or more groups based on a responsiveness of each population of cells to each agent. In particular aspect, the ATM, Chk2 and p53 genes are targeted. In other aspects, the p53, ATR, Chk1, Chk2, Smg-1, DNA-PKcs, Bok and Bim genes are targeted.

As will be appreciated by those of skill in the art, the article of manufacture can be used, for example, to screen a library of agents for an agent having a chemotherapeutic or genotoxic effect.

EXEMPLIFICATION

A Mammalian Functional-Genetics Approach to Characterizing Cancer Therapeutics
Methods
Cell Lines and Drugs Eμ-Mycp19$^{Arf-/-}$ mouse lymphoma cells were cultured in B cell medium as described (Schmitt, C. A., et al., *Genes Dev*, 13:2670-2677 (1999)). MM1S and RPMIB226 cells were cultured in RPMI medium supplemented with glutamate and 10% (v/v) FBS. Drugs were obtained from Sigma, Tocris, Calbiochem, VWR, LC Laboratories and other suppliers. shRNA vectors were generated as described (Dickins, R. A. et al. Nat. Genet, 37, 1289-1295 (2005); Jiang, H. et al. Genes Dev. 23, 1895-1909 (2009)). P185+p19$^{Arf-/-}$ acute lymphoblastic leukemia cells were derived and cultured according to the procedures outlined in ref. 35.
Drug Treatment and Flow Cytometry Eμ-Mycp19$^{Arf-/-}$ cells were counted and seeded at 1 million cells per ml in 48-well plates and treated with various concentrations of drugs. To approximate therapeutic situations in which drug dose decreases over time, half of the volume from each experiment was removed and replenished with fresh medium every 24 h. Cells were analyzed by fluorescence-activated cell sorting (FACS), with propidium iodide as a viability marker. LD80-90 of drugs are defined as concentrations at which the lowest viability reading out of three FACS time points (24, 48 and 72 h) is between 10% and 20%. After drug dose was determined, Eμ-Mycp19$^{Arf-/-}$ cells were infected with retroviruses encoding shRNAs targeting particular genes. Individual infected cell populations were counted and seeded at 1 million cells per ml in 48-well plates and treated with drugs using the aforementioned protocol. At 72 h, treated and untreated cells were analyzed by flow cytometry. GFP percentages of live (PI-negative) cells were recorded and used to calculate relative resistance index. To avoid outgrowth of untreated control cells, they were typically seeded them at 0.25 million per ml, and 75% of medium was replaced at 24 and 48 h.
Calculation of Relative Resistance Index (X)

To compare the relative level of chemoresistance and sensitization conferred by each gene knockdown, the concept of RI (see definition above) was introduced, to more accurately analyze the GFP competition results. The value of RI is defined as X. The biological meaning of this factor X is that in a mixture of uninfected and infected (knockdown)

cells, the infected (knockdown) cells will be X-fold as likely to survive drug treatment when compared to uninfected cells. By this definition of X, if one out of n uninfected cells survives a drug treatment, then X our of n infected cells should survive. If the total number of uninfected and infected cells are defined as T and the GFP percentage of untreated population are defined as G1, then the number of surviving, uninfected cells (un) can be defined as n−un=T×(1−G1)×1/n, and the number of surviving, infected cells (in) can be defined as n−in=Tx G1×X/n. Hence, the GFP percentage of the treated, surviving population (G2) can be calculated as G2=(n−in)/((n−un)+(n−in)). From this equation, it can be derived that X=(G2−G1×G2)/(G1−G1×G2). This equation was used in the studies to compute RI values.

Enhanced K-Nearest-Neighbors Methods

K-nearest-neighbors modeling is a weighted-voting methodology in which the proximity to the training set is used to predict drug class membership. This analysis is included for four reasons. (i) It provides independent validation of the clustering result. (ii) It allows quantification of the predictive power of the reference set through leave-one-out-cross-validation. (iii) Leave-one-out cross-validation allows performance of a feature reduction to discover smaller gene sets. (iv) It provides an objective prediction of classes for new compounds.

K-nearest-neighbors predictions were performed using a correlation-based metric and a consensus voting scheme. The MATLAB knnclassify.m function was used as a basis for the feature reduction search, as well as cross-validation and predictions. The cross-validation for the K-nearest-neighbors approach was done by systematically leaving out one of the 18 drugs at a time in the final dataset (FIG. 1c) and using the remaining 17 to predict the left-out drugs' identities.

To reduce the size of the feature set to a smaller group of key shRNAs, a subset of 2,000 unique shRNA sets of increasing size were randomly searched. Sampled subsets were scored on the basis of their ability to cross-validate. As much more extensive search (>50,000 subsets) of eight shRNA signatures that would be able to correctly classify all of the drugs in the reference set was then performed. The shRNA subsets that cross-validated at 100% were then ranked by their least-squares correlation with the distances between drugs in the 29-shRNA signature, and the eight-shRNA set with the highest correlation score was chosen for later experiments.

A K-nearest-neighbors-based approach will always yield a prediction of drug class on the basis of proximity. Therefore, to evaluate the similarity of a new drug to its predicted class a linkage ratio p-value test was developed. Briefly, the initial cluster size of each of the seven drug groups was calculated (FIG. 1c) by evaluating the average of all pairwise linkage distances amongst all members of a drug group. When a test compound was predicted to belong to a drug group on the basis of proximity, then the cluster size of that particular drug group was calculated again with the new test drug included. A linkage ratio was then calculated by comparing the cluster size with and without the tested compound. A linkage ratio of less than one indicated that the addition of the drug to a cluster made the average distance between drugs in that category smaller, whereas a linkage ratio greater than one indicated that the cluster expanded. An obvious tradeoff exists between cluster expansion to accommodate modestly distinct compounds with highly homologous mechanisms and expanding the definition to a point where one masks the existence of a completely new compound. This tradeoff varies among drug classes as a function of the inter-class distances. To estimate the significance of a K-nearest-neighbors prediction, as well as to determine whether a compound had a mechanism of action different from those of the original seven drug groups, the negative control distributions of drug classifications were sampled. This was done on a class-by-class basis by taking the previously studied compounds and forcing them to erroneously classify. A linkage ratio for all of these erroneous classifications was then calculated. On a class-by-class basis a normal distribution was fit to the range of misclassified linkage ratios. The value of the cumulative distribution function was used to calculate the p-value of the new classifications (FIG. 5c), using the null hypothesis that the linkage ratio for a prediction is identical to the linkage ratios of the negative control distribution. The complete MATLAB algorithm used to perform this analysis is provided as the "Drug Prediction Score.M" file found at web.mit.edu/icbp/data/index.html.

Clustering: Agglomerative Hierarchical Clustering was Performed in Matlab v7.0.

All RI values were Log 2 transformed to represent depletion and enrichment data on the same scale. To measure the distance between clusters, an inverse correlation based metric was used: After all drug pairwise distances were calculated, centroid linkage was used to compute the distance between cluster groups. Several forms of significance calculations were performed. To estimate the overall number of significant underlying drug groups in the data set, the number of latent variables that could explain the majority of the variance in the data set via a principal components analysis was analyzed. However, Random Matrix Theory for small data sets suggests that small noisy data sets may have large eigenvalues based upon chance. Therefore, in order to estimate the significance of the categorization of underlying drugs, a Monte Carlo analysis on our dataset was performed. Briefly, 1000 data matrices from our drug-gene data were sampled. Then the distribution of the cumulative variance explained by our 7-component model relative to randomized matrices was plotted. This Monte Carlo analysis estimated the significance of the number of components that one uses to interpret the PCA model.

In an idealized scenario where the distances between and within drug clusters are similar across drug types, a uniform cutoff at a single branch length should guide interpretation of the clusters. However, in stratified datasets described herein, where considerable variation exists within and between clusters, a more stratified approach becomes appropriate. The DNA damage drug set contained extraordinarily close correlations between distinct drugs relative to the rest of the dataset. To determine whether sub-categories of drugs within this cluster could be confirmed, the PCA sampling approach was extended to this subset of data. Utilizing this stratified approach to cluster interpretation, a hypothesis of three distinct DNA damage sub-clusters was supported. This variegated approach to cluster interpretation was also evaluated by doing Bootstrapping analysis in R using the PVClust function (Suzuki, R & Shimodaira, H., Bioinformatics, 22, 1540-1542 (2006)). This approach was used to complement the PCA data. The PCA data indicate how many significant underlying drug variables one can interpret from the data, and the bootstrapping indicated whether particular branches were significant.

```
function [class, normpvalue, predlr] = DrugPredictionScore(training, test, groups,
numbern)
% This function takes as an argument a (training) set that has
% observations(drugs)as rows and variables as columns, (test) is a test vector to
classify using
% training and in this version is limited to n=1. (groups) is a column vector
% of group memberships(that are sequential and numeric starting at n=1). Note if you
have 7 groups they must be ordered 1-7 for
% the observations in (training). Numbern is the
% number of nearest neighbors to include, the default is majority rule. The class is
the predicted group
% mebership in test, and pvalue is the predicted significance of the
% inclusion of the test compound in the predicted class
% Currently a KNN classifier is hardcoded into the algorithm, but the
% algorithm can be used with any matlab multi-class classifier if the code
% is changed. In our shRNA dataset we have noted that Naive-Bayes
% Classifiers perform similarly well. In either case a euclidean metric of
% cluster size is used to assess significance.
%Step1 creating the reference distances and null distributions
%_____
%_____
DistanceMatrix=squareform(pdist(training,'euclidean'));
M=max(groups)
i=1
nulldist={ }
ALtot=[ ]
while i< M+1
    j=1%makes an index that terminates when the max group number is reached
    AL=[ ]
    gpos=[ ]
    nongpos=[ ]
    while j< length(groups)+1 %looks through the groups vector sequentially to
determine which entries match the group label i
        if groups(j,1)==i %sequentially checks the equality
            gpos=horzcat(gpos,j)%horizontally concatenates the reference row for a given
group.
        elseif groups(j,1)~=i
            nongpos=horzcat(nongpos,j)
        end
        j=j+1
    end
    S=length(gpos)
    Sn=length(nongpos)
    submati=[DistanceMatrix(gpos(1,1):gpos(1,S),gpos(1,l):gpos(1,S))]%builds submatrix
of group specific distances and then calculates the averages on the basis of this
    AL=sum(sum(submati))/(S*(S-1))
    ALtot=horzcat(ALtot,AL)
    k=1
    newalvec=[ ]
    while k < Sn+1 %this step build null distributions based on the empircal prediction
using false negatives
        alldistances=DistanceMatrix(nongpos(I,k),:)
        l=1
        nullpredictionsdist=[ ]
        while l < S+1
            nullpredictionsdist=vertcat(nullpredictionsdist,alldistances(1,gpos(1,l)))
            l=l+1
        end
        newal=(sum(sum(submati))+sum(nullpredictionsdist))/((S*(S-1))+S)
        newalvec=vertcat(newalvec,newal)
        k=k+1
    end
    storednull{1,i}=newalvec
    i=i+1
end
%_____
%step2 is the prediction of drug class and updating a new training set to
%take into account that prediction, and then calculating the average
%linkage following the inclusion of the test drug
%_____
training2=training
test2=test
groups2=groups
class=knnclassify(test, training, groups, numbern, 'euclidean')
m=1
while m < length(class)+1
    n=1
    while n < length(groups)+1
        if groups(n,1)==class(m,1)
            it n<length(groups)
                trainingnew=vertcat(training2(1:n,:),test2(m,:),training2(n+1,:))
```

-continued

```
                    groupsnew=vertcat(groups2(1:n,:),class(m,:),groups2(n+1,:))
            elseif n==length(groups)
                    trainingnew=vertcat(training2(1:n,:),test2(m,:))
                    groupsnew=vertcat(groups2(1:n,:),class(m,:))
            end
        end
        n=n+1
    end
    m=m+1
end
DistanceMatrixnew=squareform(pdist(trainingnew,'euclidean'))
Mnew=max(groupsnew)
i=1
ALnew=[ ]
while i< Mnew+1
    j=1%makes an index that terminates when the max group number is reached
    AL2=[ ]
    gposnew=[ ]
    nongposnew=[ ]
    while j< length(groupsnew)+1 %looks through the groups vector sequentially to
determine which entries match the group label i
        if groupsnew(j,1)==i %sequentially checks the equality
            gposnew=horzcat(gposnew,j)%horizontally concatenates the reference row for a
given group.
        elseif groupsnew(j,1)~=i
            nongposnew=horzcat(nongposnew,j)
        end
        j=j+1
    end
    Snew=length(gposnew)
    Snnew=length(nongposnew)
submatinew=[DistanceMatrixnew(gposnew(1,1):gposnew(1,Snew),gposnew(1,1):gposnew(1,Snew)
)]%builds submatrix of group specific distances and then calculates the averages on the
basis of this
    AL2=sum(sum(submatinew))/(Snew*(Snew-1))
    ALnew=horzcat(ALnew,AL2)
    i=i+1
end
%_____
%_Step3 is comparing to the background distribution
%1st calculate for the group predicted in class, what is the distribution of
%linkage ratios for the given group, calculate from altot(yourclass) and
%the classes entry in storednull what the distribution of increases for
%null(false) predictions are. Then calculate the linkage ratio alnew/altot
%then get pvalue
%_____
lrdist=[ ]
p=1
while p < length(storednull{1,class})+1
    lrdist=vertcat(lrdist,(storednull{1,class}(p))/ALtot(1,class))
    p=p+1
end
predlr=ALnew(1,class)/(ALtot(1,class))
lr=lrdist
lr = lr(:);
% Set up figure to receive datasets and fits
f_ = clf;
figure(f_);
set(f_,'Units','Pixels','Position',[547.333 181 680 475.45]);
legh_ = [ ]; legt_ = { };    % handles and text for legend
ax_ = newplot;
set(ax_,'Box','on');
hold on;
% ---- Plot data originally in dataset "lr data"
t_ = ~isnan(lr);
Data_ = lr(t_);
[Y_,X_] = ecdf(Data_,'Function','cdf'...
     ); % compute empirical function
h_ = stairs(X_,Y_);
set(h_,'Color',[0.333333 0 0.666667],'LineStyle','-', 'LineWidth',1);
xlabel('Data');
ylabel('Cumulative probability')
legh_(end+1) = h_;
legt_{end+1} = 'lr data';
% Nudge axis limits beyond data limits
xlim_ = get(ax_,'XLim');
if all(isfinite(xlim_))
    xlim_ = xlim_ + [-1 1] * 0.01 * diff(xlim_);
    set(ax_,'XLim',xlim_)
```

```
end
x_ = linspace(xlim_(1),xlim_(2),100);
%
% ---- Create fit "fit 1"
%
% Fit this distribution to get parameter values
t_ = ~isnan(lr);
Data_ = lr(t_);
% To use parameter estimates from the original fit:
%   p_ = [ 5.5, 3.027650354097];
pargs_ = cell(1,2);
[pargs_{:}] = normfit(Data_, 0.05);
p_ = [pargs_{:}];
y_ = normcdf(x_,p_(1), p_(2)); % compute cdf
h_ = plot(x_,y_,'Color',[1 0 0],...
        'Linestyle','-', 'LineWidth',2,...
        'Marker','none', 'MarkerSize',6);
legh_(end+1) = h_;
legt_{end+1} = 'fit 1';
hold off;
leginfo_ = {'Orientation', 'vertical', 'Location', 'Northwest'};
h_ = legend(ax_,legh_,legt_,leginfo_{:});   % create legend
set(h_,'Interpreter','none');
normpvalue=normcdf(pred1r,p_(1), p_(2))
%this works
```

Comparison of shRNA's to miRNA's

Local sequence alignments were performed in matlab using the localalign.m function. Briefly, each shRNA in the 8 shRNA signature was pairwise aligned to every miRNA in the Mus musculus genome.

Results

Clustering Drugs Via shRNA-Mediated Phenotypes

As described herein, it was hypothesized that RNAi-mediated suppression of cell death regulators in mammalian cells would uniquely affect the cellular response to certain types of drugs and that drugs with similar mechanisms of action would elicit similar shRNA-dependent responses. To test this strategy, a cell line derived from tumors from a well-established mouse model of Burkitt's lymphoma was used (Adams, J. M. et al. Nature 318, 533-538 (1985); Schmitt, C. A., et al., Genes Dev. 13, 2670-2677 (1999)). This cell line was chosen as an experimental system for two reasons. First, these cells are highly sensitive to a diverse set of chemotherapeutics, allowing small molecules to be used at pharmacologically relevant doses. Second, like many high-grade lymphomas, these cells undergo rapid apoptosis, as opposed to prolonged cell cycle arrest, following treatment. This common biological outcome after treatment allows for a systematic comparison of drugs.

Figure 7A:
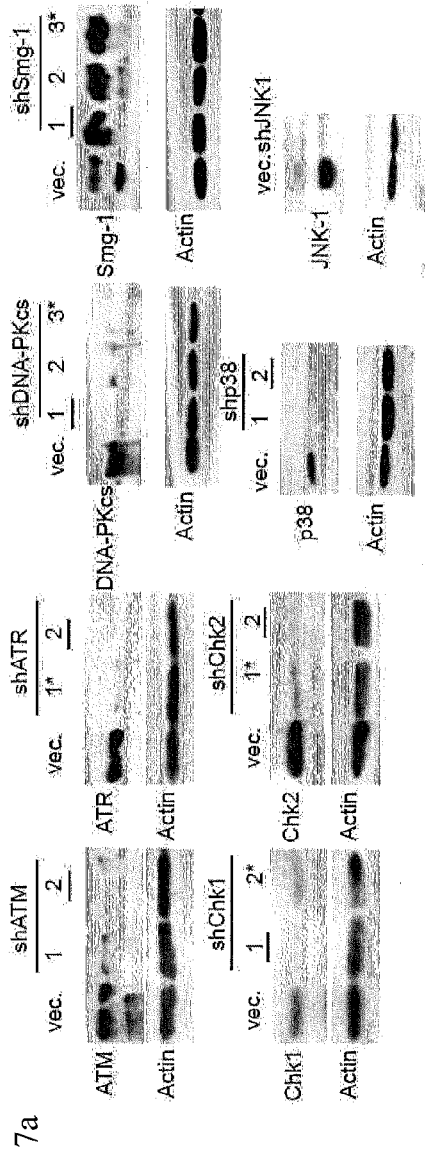
FIGS. 7a-7b: shRNAmir-mediated stable suppression of drug response genes. 7a, Western blot image showing knockdown of p53-activating kinases. Underlined lanes demarcate shRNAs used in subsequent studies. Starred lines demarcate shRNAs used in FIG. 4c as additional shRNAs. 7b, QPCR data showing knockdown of Bcl2 family genes. Data represent the results from two independent experiments. Bcl2 and Mcl1 were omitted from this study, as Bcl2 and Mcl1 stable knockdown cells could not be established.
Figure 7B:
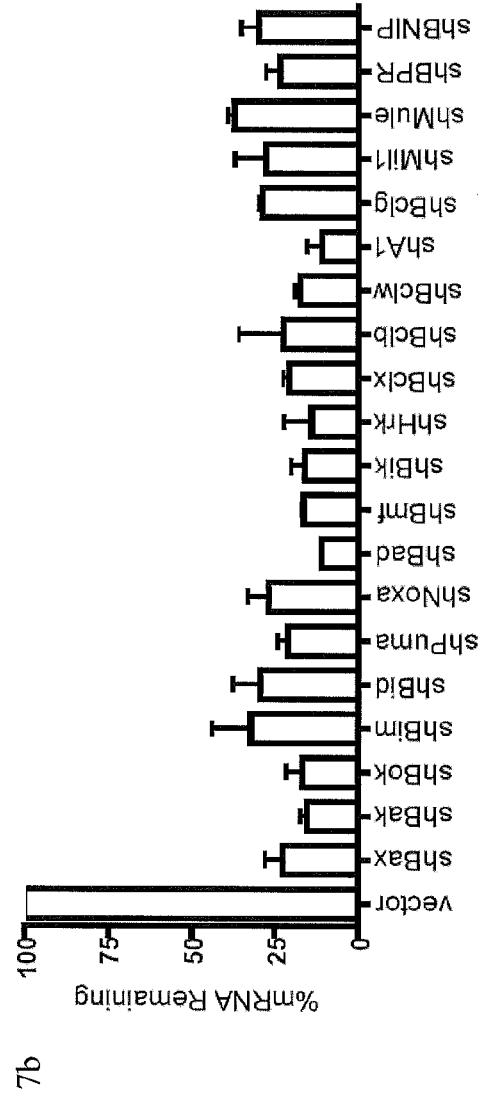

In determining which genes to knock down for the studies, two classes of genes known to be critical for cell fate decisions after drug treatment were chosen. The Bcl2 family of genes includes both central mediators and inhibitors of cell death, and different members of this gene family are involved in the response to distinct cell death stimuli (Schmitt, C. A., et al., Genes Dev. 13, 2670-2677 (1999); Youle, R. I. & Strasser, Nat. Rev. Mol. Cell. Bioi. 9, 47-59 (2008)). The transcription factor p53 functions upstream of components of the Bcl2 family and is another important cell death regulator (Lu, C. & EI-Deiry, W. S. Apoptosis 14, 597-606 (2009)). Mutation or deletion of p53 has been shown to affect the cellular response to many types of chemotherapeutic drugs (Lowe, S. W. et al., Cell 74, 957-967 (1993); Lowe, S. W. et al. Science 266, 807-810 (1994)). As the stabilization and activity of p53 is strongly regulated by phosphorylation, a panel of p53-activating kinases, including ATM, ATR, Chk1, Chk2, DNAPKcs, Smg-1, JNK1 and p38 was also targeted (Bode, A. M. & Dong. Z. Nat, Rev. Cancer 4, 793-805 (2004); Brumbaugh, K. M. et al. Mol. Cell 14, 585-59B (2004)). Importantly, aside from their roles as regulators of p53, these kinases are also involved in additional cellular responses to chemotherapy, such as DNA replication and repair, the activation' of cell cycle checkpoints, regulation of RNA stability and stress signaling (Lavin, M. P. Nat. Rev. Mol. Cell. Bioi. 9, 759-769 (2008); Cimprich, K A. & Cortez, D, Nat. Rev. Mol. Cell. Biol. 9, 616-627 (2008); Bartek, J. & Lukas, J. Cancer Cell 3, 421-429 (2003); Reinhardt, H. C, et al., Cancer Cell 11, 175-189 (2007); Pearce, A. I. & Humphrey, T. C. Trends Cell Biol. 11, 426-433 (2001)). Thus, shRNA vectors targeting the Bcl2 family, p53 and its activating kinases were generated (Supplementary Results, FIGS. 7a-7b and Table 2).

Figure 1B:
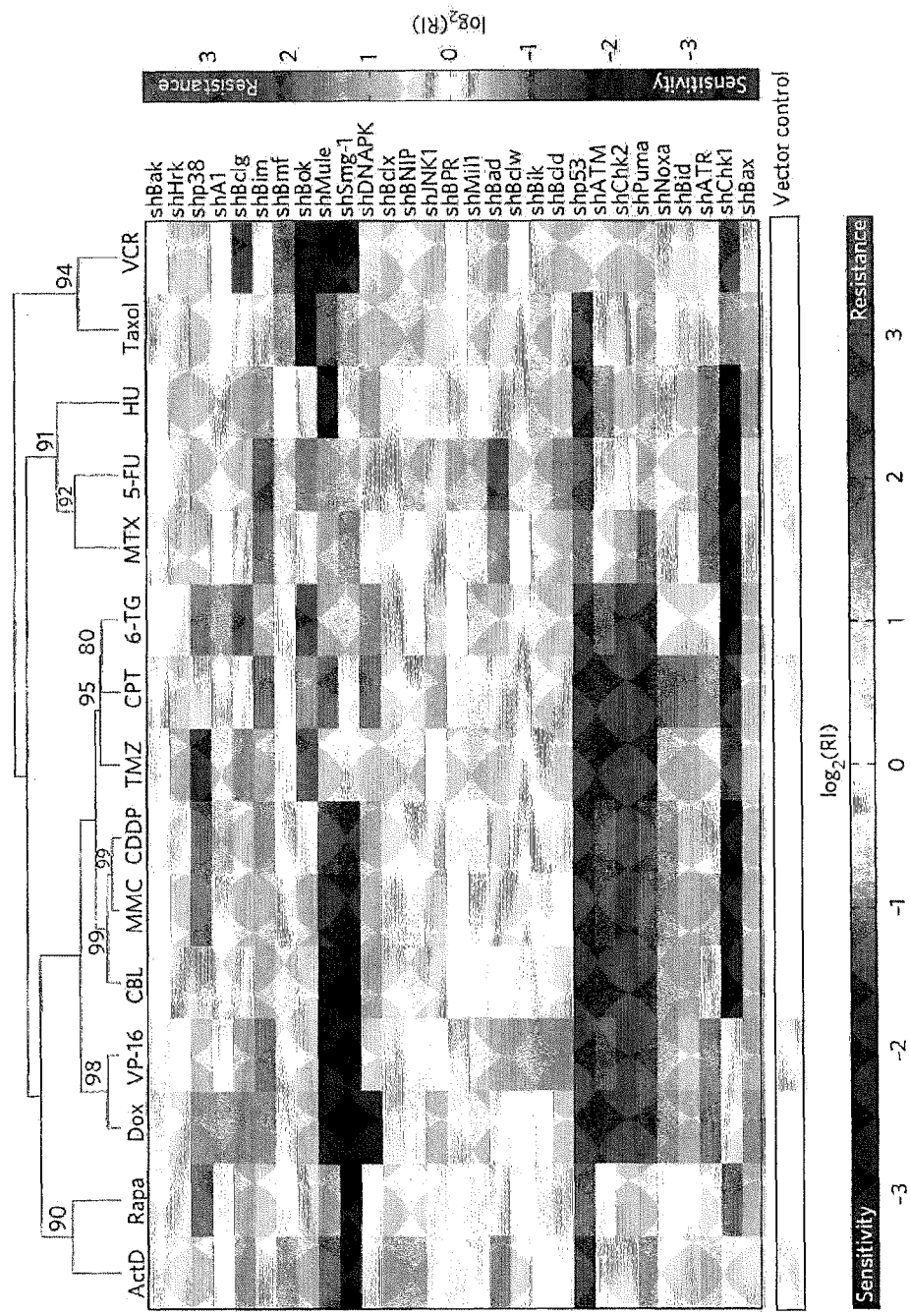
Figure 8A:
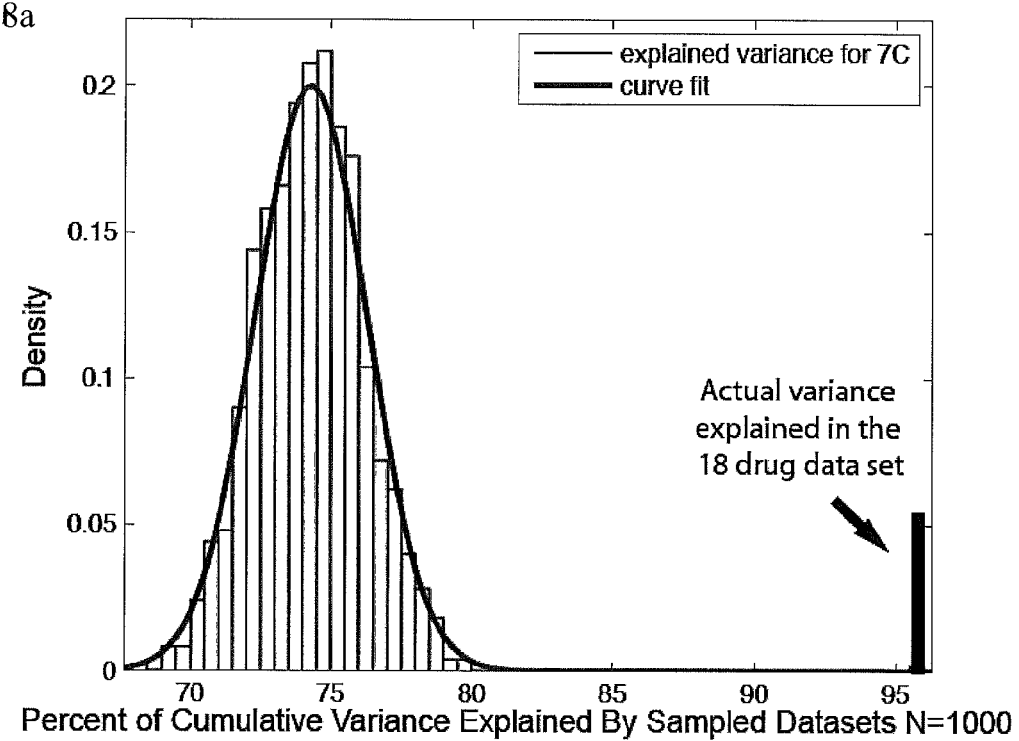
FIGS. 8a-8b: Significance analysis of the 18 drug and DNA damage subcategory clustering. 8a, PCA Monte Carlo analysis comparing the percent variance explained in the actual 7 category (7C) decomposition of the 18-drug set versus 7C decomposition of 1000 randomized data sets. 8b, PCA Monte Carlo analysis comparing the percent variance explained in the actual 3 category (3C) decomposition of the DNA damage set versus 3C decomposition of 1000 randomized data sets.
Figure 8B:
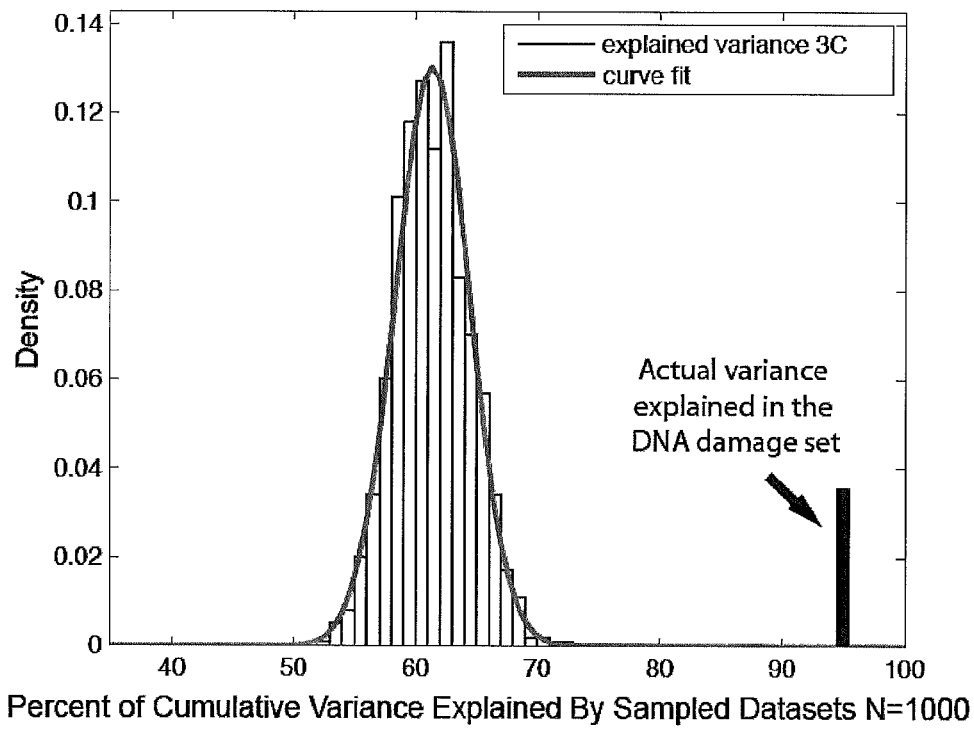

To enable a quick and accurate analysis of how the suppression of a given gene affects drug-induced cell death, a single-cell flow cytometry-based GFP competition assay was used. Lymphoma cells were infected with retroviruses coexpressing a given shRNA and green fluorescent protein (GFP) and subjected to 72 h of drug treatment (FIG. 1a). In this assay, GFP-negative cells in the same population serve as an internal control. Using this approach, how suppression of individual genes affected drug-induced cell death was systematically investigated. As an initial proof of principle, 15 chemotherapeutics representing major categories of anti-cancer drugs in clinical use were chosen. To compare different drugs using an objective criterion, all drugs were used at their LD80-90-a concentration at which 80-90% of uninfected lymphoma cells were killed (Table 3). A control retrovirus lacking an shRNA or retroviruses expressing shRNAs targeting 29 genes were individually used to infect lymphoma cells. Each infected population was separately treated with 15 chemotherapeutic drugs, and the effect of a particular gene knockdown on therapeutic response was compiled as values of the GFP-determined 'resistance index' (RI) (FIG. 1b). Drugs with similar mechanism of action were expected to have similar patterns of genetic dependence on these 29 genes, which would manifest as similar patterns of RI values. To test this hypothesis in an unbiased manner, an unsupervised agglomerative hierarchical clustering approach was used to compare the RI values of different drugs (FIG. 1b). The significance of this hypothesis was then evaluated using a Monte Carlo principal components analysis-based method (Pritchard, J. R. et al. Mol. Cancer. Ther. 8, 2183-2192 (2009)). Notably, all 15 drugs tested in this initial experiment formed six distinct clusters that were consistent with their molecular mechanisms of action (FIGS. 8a-8b). Specifically, clear groupings were seen between topoisomerase II (TopoII) poisons doxorubicin (Dox) and etoposide (VP-16), DNA cross-linking agents cisplatin (CDDP), mitomycin C (MMC) and chlorambucil (CBL), single-strand break (SSB)-inducing agents camptothecin (CPT), 6-thioguanine (6-TG) and temozolomide (TMZ) (Swann, P. P. et al. Science 273, 1109-1111 (1996); Mojas, N., et al., Genes Dev. 21, 3342-3355 (2007)), nucleic acid synthesis inhibitors methotrexate (MTX), 5-fluorouracil (5-FU) and hydroxyurea (HU), and spindle poisons vincristine (VCR) and paclitaxel (Taxol). Taken together, these data showed that a simple comparison of drug response in cells expressing a small set of shRNAs could effectively categorize established chemotherapeutic drugs into subgroups that demarcate common target proteins and pathways.

Figure 1C:
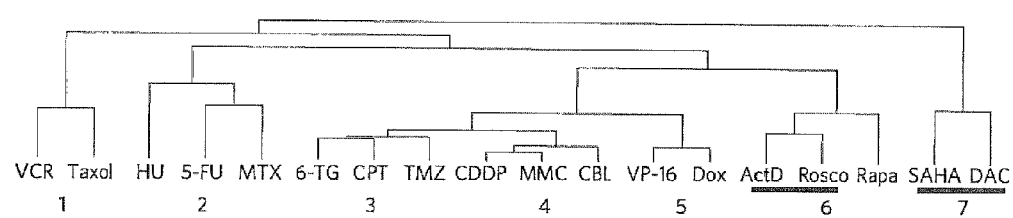
Figure 1D:
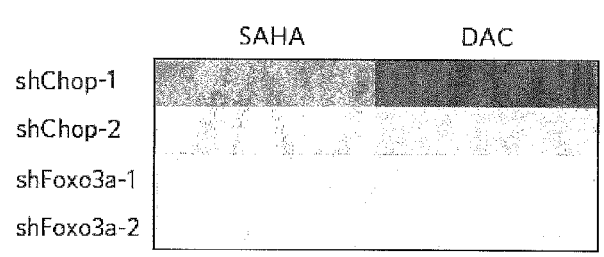
Figure 9A:
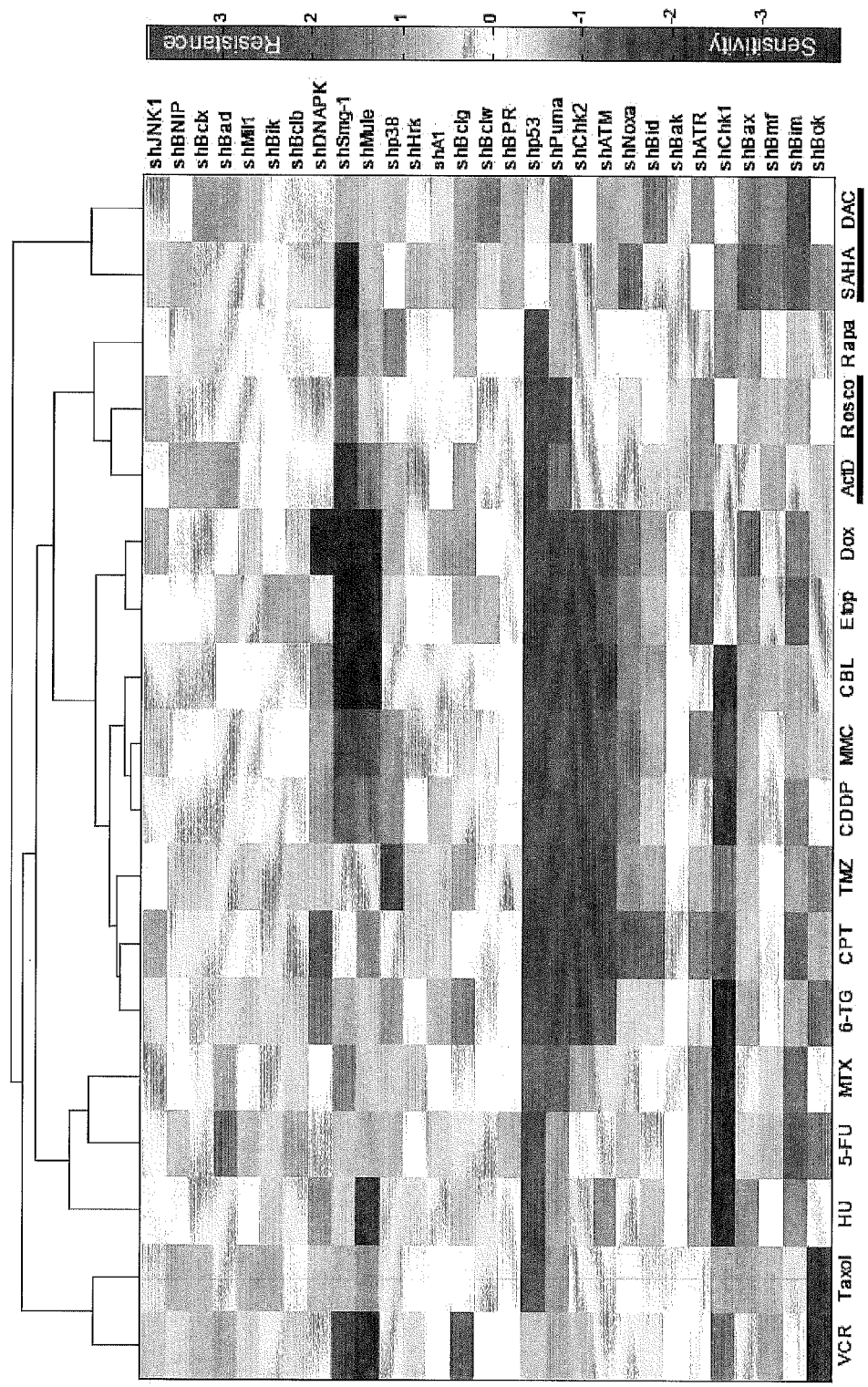
FIGS. 9a-9b: 9a, Unsupervised clustering of R1 values of the 15 reference compounds, SAHA, decitabine (DAC), and roscovitine (Rosco). Agglomerative hierarchichal clustering was performed on log transformed RI values for these 18 drugs, using a correlation metric and centroid linkage. Their cluster position is underlined in red. 9b, Lymphoma cells were treated with SAHA or DAC for 6 or 9 hours. Bim expression level was analyzed by western blot.
Figure 9B:
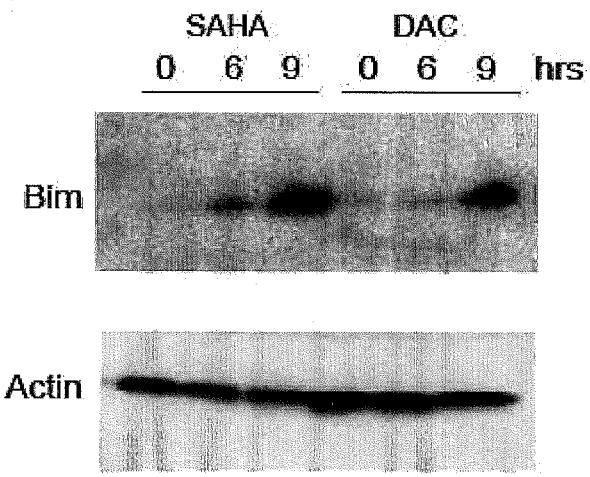

To investigate whether this platform could be used to characterize mechanisms of drug action, several recently developed chemotherapeutics were examined: suberoylanilide hydroxamic acid (SARA), decitabine and roscovitine. Although the immediate biochemical targets of these new chemotherapeutics are known, the mechanisms of cell death induced by these drugs are less well defined. Using the RNAi-based approach, RI values for each of these three drugs were compiled and compared with the 15 reference drugs mentioned earlier. It ws observed that the CDK inhibitor roscovitine (Rosco) was most similar to the RNA polyinerase inhibitor actinomycin D (ActD) (FIG. 1c and FIGS. 9a). This is consistent with the findings of several studies showing that roscovitine inhibits CDK7, a component of the general transcription factor TFIIH, to inhibit RNA transcription (Akhtar, M. S. et al. Mol Cell 34, 387-393 (2009); Ljungman, M. & Paulsen, M. T. Mol Pharmacal. 60, 785-789 (2001); MacCallum, D. E. et al. Cancer Res. 65, 5399-5407 (2005)). Notably, the HDAC inhibitor SAHA and the DNA methyltransferase inhibitor decitabine (DAC) formed a distinct cluster outside of the 15 reference drugs (FIG. 1c), indicating that these two drugs may share a similar mechanism of cell death. To extract the most relevant genes for distinguishing the SABA-DAC cluster, shRNAs were ranked upon their ability to classify this cluster relative to the rest of the dataset. The most unique aspects of the new SAHA-DAC cell death signature were the (i) p53-independence ($\log_2 RI \approx 0$) and (ii) Bim-dependence ($\log_2 RI \approx 2$) of cell death, consistent with previous studies of SABA treatment in mouse lymphoma models (Lindemann, R. K et al. Proc. Natl. Acad. Sci. USA 104, 8071-8076 (2007)). Indeed, both SABA and DAC treatment resulted in an increase in the levels of the proapoptotic BH3-only protein Bim (Supplementary FIG. 3b). Furthermore, suppression of the Bim transcription regulator Chop, but not Foxo3a, resulted in resistance to both SAHA and DAC (FIG. 1d). Thus, the RI patterns of these newly established drugs could effectively identify their mechanism of action.

Functional Characterization of Derivatized Compounds

Figure 2C:
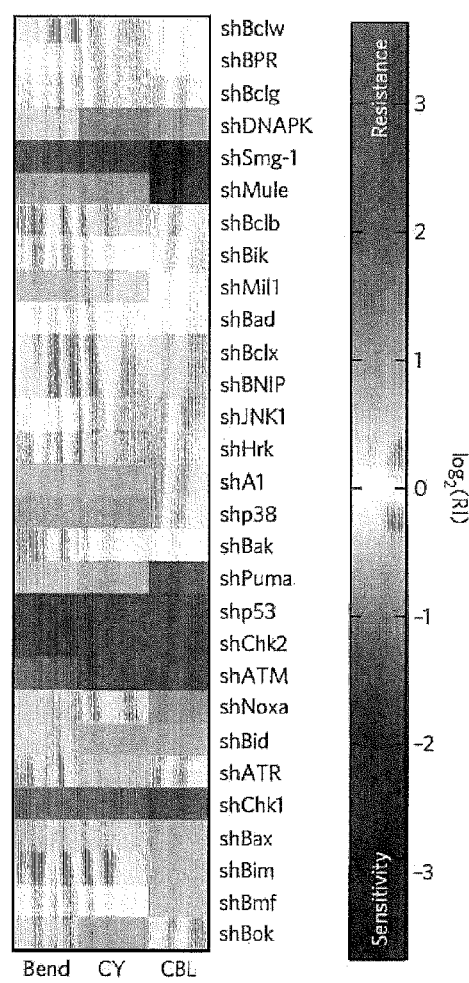
Figure 2D:
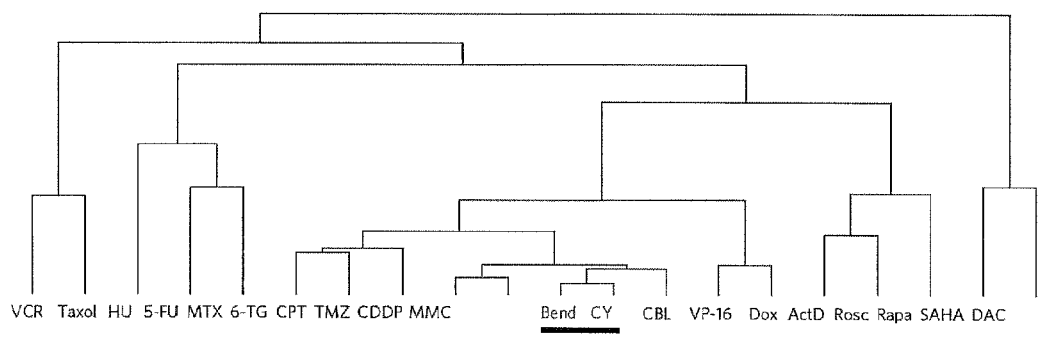

A significant challenge in drug development is determining whether lead compound derivatives with enhanced efficacy share the same mechanism of action as the original small molecule. Theoretically, derivatized compounds could show enhanced efficacy, owing to either the activation of additional cell death pathways or, alternatively, through altered pharmacodynamic properties. To examine whether our approach could be used to differentiate between these possibilities, an shRNA-based functional analysis of CY190602, a chemical derivative of the nitrogen mustard bendamustine was performed (FIG. 2a). Compared to the parental drug, CY190602 showed approximately 20-100-fold enhanced toxicity toward cells from patients with multiple myeloma (FIG. 2b), an indication for which bendamustine is currently in clinical use. However, the mechanism underlying this increase in cytotoxicity remains unclear. Notably, CY190602's modification on bendamustine occurs on a side chain well away from the nitrogen mustard functional group. To address whether CY190602's toxicity could still be attributed to the nitrogen mustard or whether it was a result of altered target specificity caused by the side chain modification moieties, the RI values of bendamustine and CY190602 were compiled and compared to those of the 18 reference drugs. Notably, bendamustine and CY190602 showed highly similar patterns of RI values (FIG. 2c), despite a 100-fold-lower dose of CY190602. Additionally, both drugs clustered together with chlorambucil, another nitrogen mustard (FIG. 2d), and a supervised K-nearest-neighbors approach (see Methods for a detailed rationale) predicted a chlorambucil-like mechanism for both drugs. This indicated that the primary mode of action of CY190602 is nitrogen mustard-mediated DNA damage rather than an off-target effect conferred during drug optimization.

Screening for Compounds on the Basis of snRNA Signatures

Figures 3A, 3B:
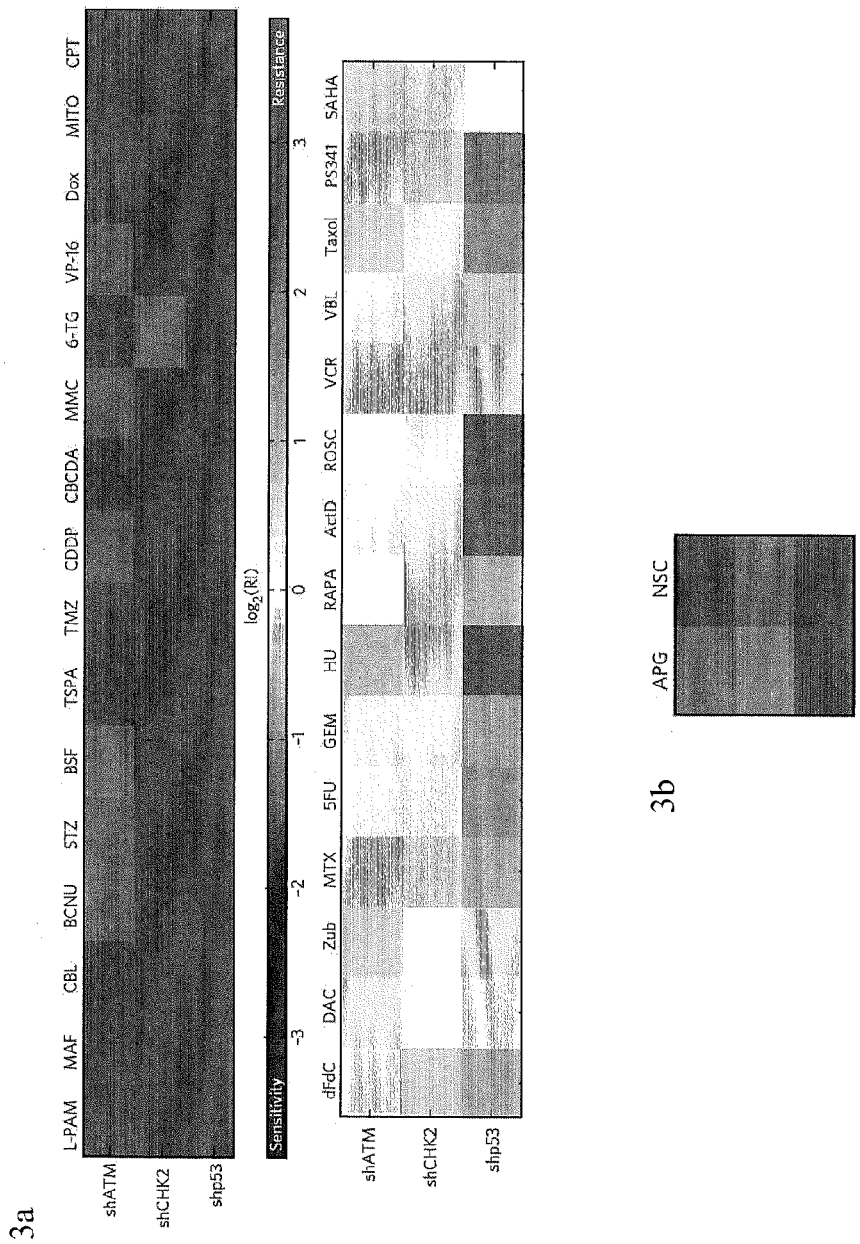
FIGS. 3a-3e: Identification and functional characterization of ill-defined genotoxic drugs. (3a) A heat map showing the response of cells expressing shATM, shChk2 or shp53 to 16 genotoxic (upper panel) and 15 nongenotoxic (lower panel) chemotherapeutics (see Supplementary Table 2 for drug abbreviations). (3b) The shATM-Chk2-p53 response signature for apigenin (APG) and NSC3852 (NSC). (3c) The branching pattern for the 18 reference compounds plus APG and NSC. APG clusters with the TopoII poisons Dox and VP-16, whereas NSC clusters with the TopoI poison CPT. (3d) A comparison of the shTopoI and shTopoII response signatures for APG and NSC3852 with response signatures derived from established TopoI (CPT and CPT11) and TopoII poisons (Dox, Mito and VP-16). Although NSC3852 and APG show response patterns characteristic of TopoI and TopoII poisons, respectively, none of the other genotoxic drugs showed either of these resistance and sensitivity patterns. (3e) A graph showing the number of surviving shTopoII, shTopoI or vector control-expressing cells 12 days after drug treatment with APG or NSC3852. In each case, one million cells were plated before treatment. Data shown are mean±s.e.m. from three Independent experiments.
Figure 3C:
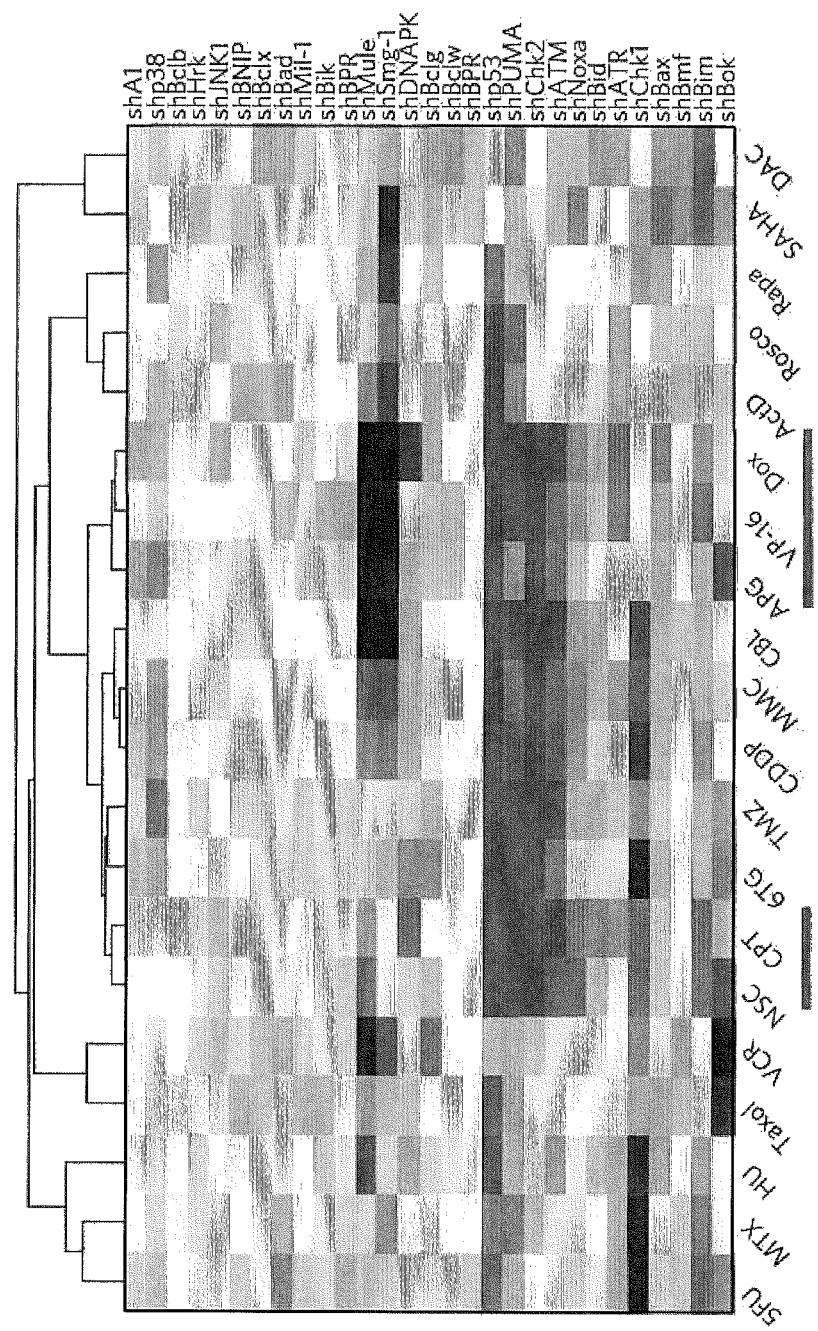
Figure 3D:
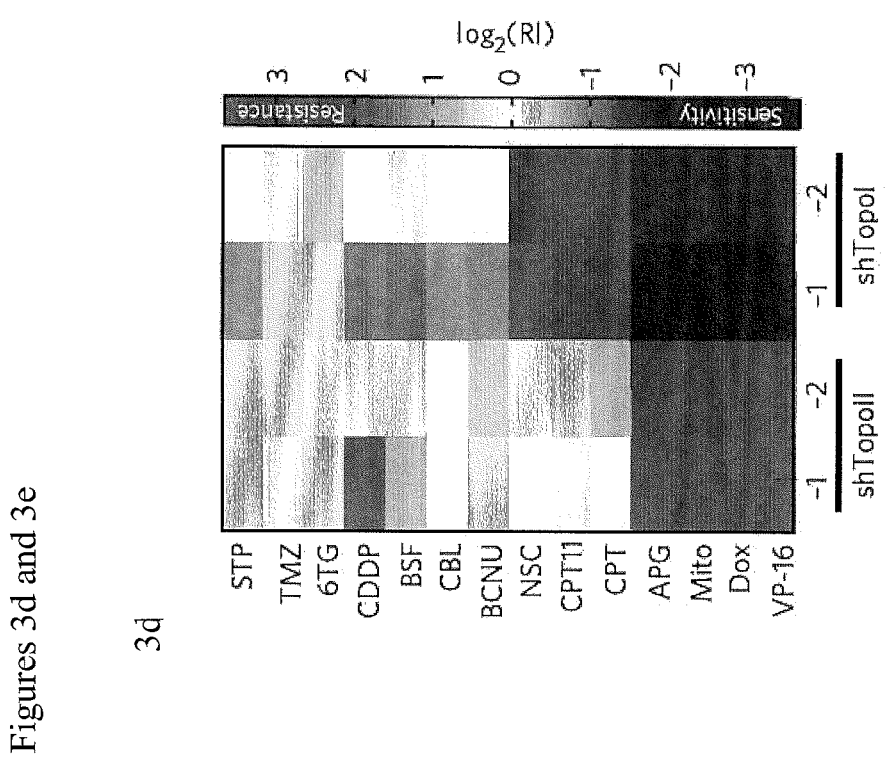
Figure 3E:
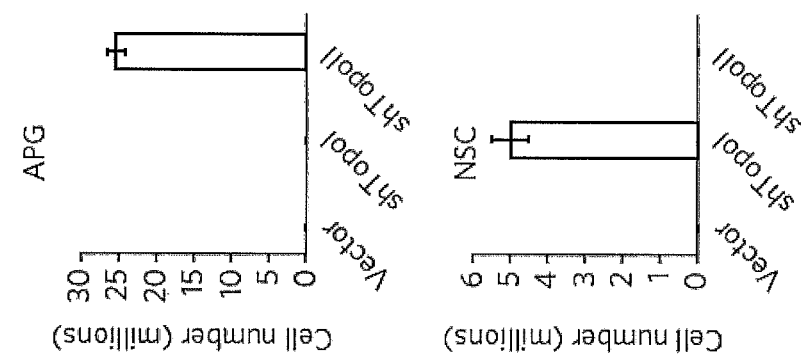
Figure 10:
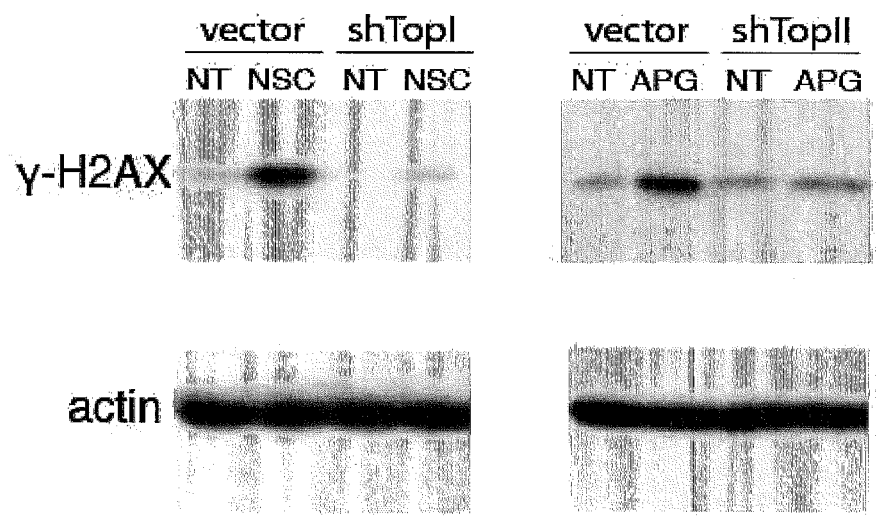
FIG. 10: The effect of TopoI and TopoII deficiency on NSC3852 and APG induced DNA damage. Vector control, TopoI and TopoII knockdown cells were treated with NSC3852 and APG, respectively. Cells were monitored by western blot for activation of a DNA damage response, as indicated by γ-H2AX phosphorylation.

Next, it was asked whether this approach could be adapted to phenotype-based screens for new drug candidates without well-established mechanisms of action. Suppression of ATM, Chk2 and p53 all led to significant resistance to genotoxic drugs such as Dox, VP-16, CPT, TMZ, 6TG, CDDP, MMC and CBL (FIG. 1b). This indicated that the shATM-Chk2-p53 'resistance signature' might be used to identify genotoxic drugs. To test this hypothesis quantitatively, whether a supervised K-nearest-neighbors approach could accurately characterize all of the drugs in the dataset as either genotoxic or nongenotoxic was examined. Indeed, when a broad panel of chemotherapeutic drugs was tested, all 16 genotoxic chemotherapeutics, but none of 15 nongenotoxic chemotherapeutics, showed a distinct shATM-Chk2-p53 resistance signature (FIG. 3a). This three-gene resistance signature was subsequently used to screen a chemical library for genotoxic compounds. Two compounds, apigenin and NSC38S2, were identified on the basis of their strong shATM-Chk2-p53 resistance signature (FIG. 3b). The full 29-gene R1 values for these two compounds were compiled and compared with reference drugs (FIG. 3c). Notably, the K-nearest-neighbors approach predicted apigenin to be most similar to the TopoII poisons doxorubicin and etoposide and NSC3852 to be most like the SSB-inducing agents. Subsequent clustering showed NSC38S2 to be most similar to the topoisomerase I (TopoI) poison camptothecin. Previous studies demonstrated that TopoII poisons are ineffective in killing TopoII-deficient cells, while showing enhanced toxicity for cells lacking TopoI (Burgess, D., et al. Proc. Natl. Acad. Sci. USA 105, 9053-9058 (2008)), Consistent with the clustering-based functional predictions, apigenin showed a pattern of shTopoII resistance and shTopoI sensitivity similar to the established TopoII poisons doxorubicin, etoposide and mitoxantrone (FIG. 3d). Conversely, NSC3852 showed a characteristic pattern of resistance, similar to established TopoI poisons camptothecin and irinotecan (CPT11). Notably, none of the other genotoxic drugs showed these resistance and sensitivity patterns with shTopoI and shTopoII (FIG. 3d). It was also found that apigenin and NSC3852 failed to induce DNA damage in TopoII- and TopoI-deficient cells, respectively (FIG. 10). Moreover, in a long-term survival assay, TopoII deficiency resulted in significant protection from apigenin, whereas TopoI deficiency significantly protected cells from NSC3852 (FIG. 3e). Taken together, these assays confirmed the classification of apigenin and NSC3852 as TopoII and TopoI poisons, respectively. Thus, small shRNA signatures can be used to screen chemical libraries to identify and characterize new compounds with particular target specificities.

An Eight-shRNA Set for Accurate Drug Mechanism Predication

Figure 4A:
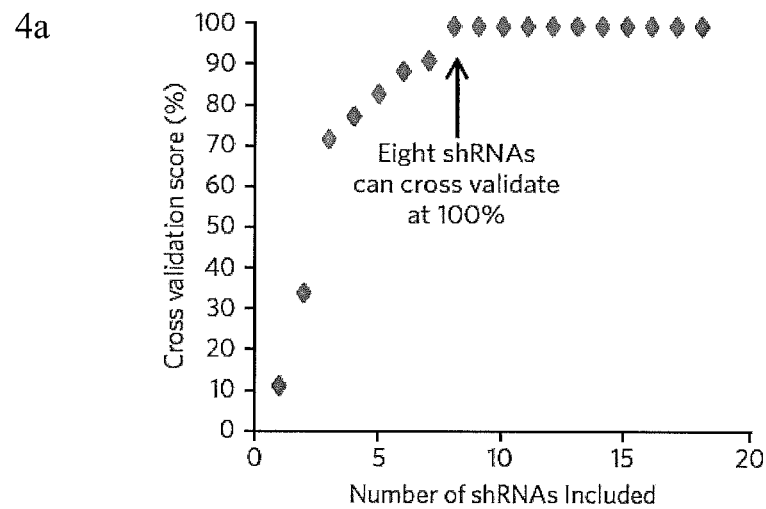
FIGS. 4a-4c: A feature reduction identifies a reduced eight-shRNA set. (4a) Analysis of the dataset used for FIG. 1c, using a randomized search strategy. The graph shows the relative efficacy of drug prediction as a function of increasing shRNA subset size, The maximum predictability for 2,000 iterations at each shRNA subset size is shown. (4b) A graph showing the correlation between enrichment or depletion of cells expressing shRNAs from the original eight-shRNA set and cells expressing shRNAs from the additional eight-shRNA set after drug treatment. Each square represents the $\log_2$RI values following single-drug treatment of cells expressing an original shRNA (x axis) or the second shRNA targeting the same gene (y axis). The slope of the best fit line is 0.64, indicating that the absolute RI values are consistently lower in cells expressing hairpins from the second eight-shRNA set. (4c) A heat map showing the relative enrichment or depletion of a second set of shRNAs (labeled with asterisks) targeting each of the genes in the eight-shRNA signature, The associated dendograms show clustering between shRNA pairs, as well as clustering of small molecules into the same seven categories predicted from the 29-shRNA signature. (d) A graph showing the correlation between enrichment or depletion of cells expressing shRNAs from the original eight-shRNA set and cells expressing shRNAs from the additional eight-shRNA set after drug treatment. Each square represents the log 2RI values following single-drug treatment of cells expressing an original shRNA (x axis) or the second shRNA targeting the same gene (y axis). The slope of the best-fit line is 0.64, indicating that the absolute RI values are consistently lower in cells expressing hairpins from the second eight-shRNA set.
Figure 11A:
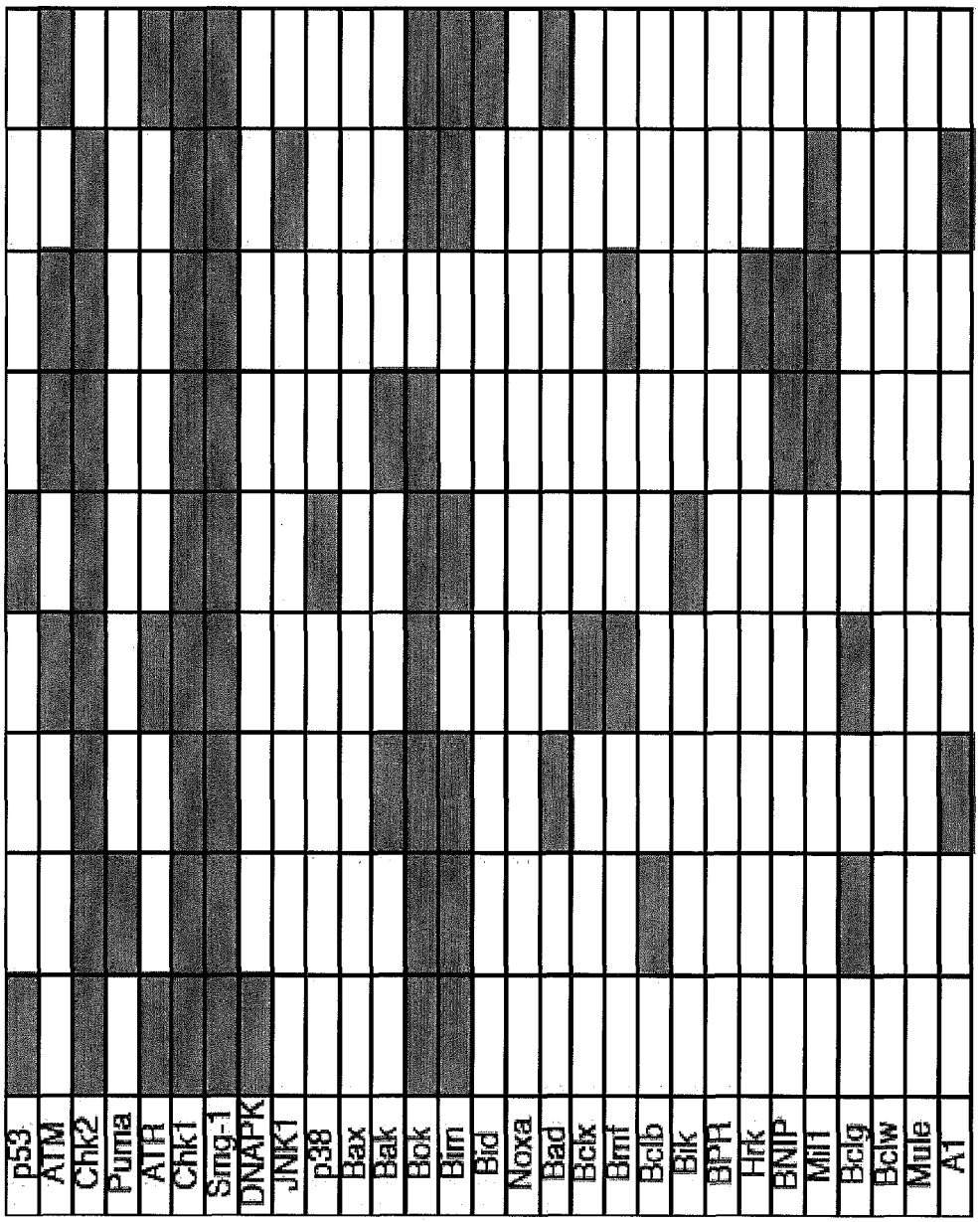
FIGS. 11a-11c: 11a, "8-shRNA signatures" that exhibit a 100% cross-validation rate. The columns show the composition of each 8-shRNA set that cross validates at 100%. Grey boxes indicate the presence of an shRNA in a particular 8-shRNA set. 11b, A scatter plot of the correlation between the pairwise distances in the reference drug set for the original 29 shRNA set versus the reduced 8 shRNA set (r2=0.81). 11c, A clustergram of 17 references drug plus APG, NSC3852, bendamustine and CY190602 using 8 shRNAs.
Figure 11B:
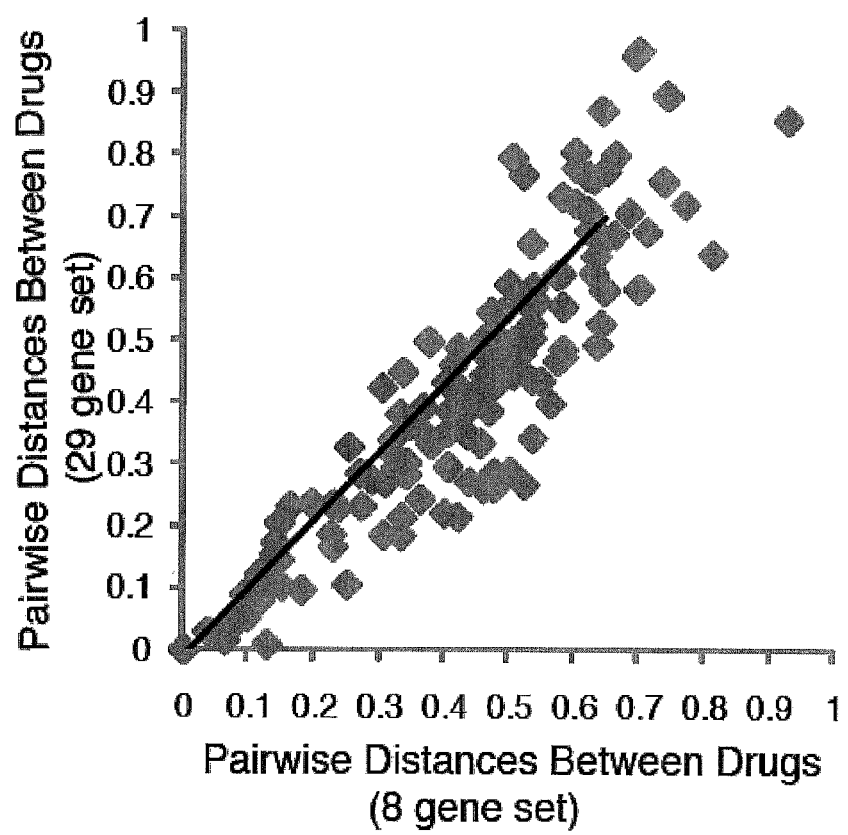
Figure 11C:
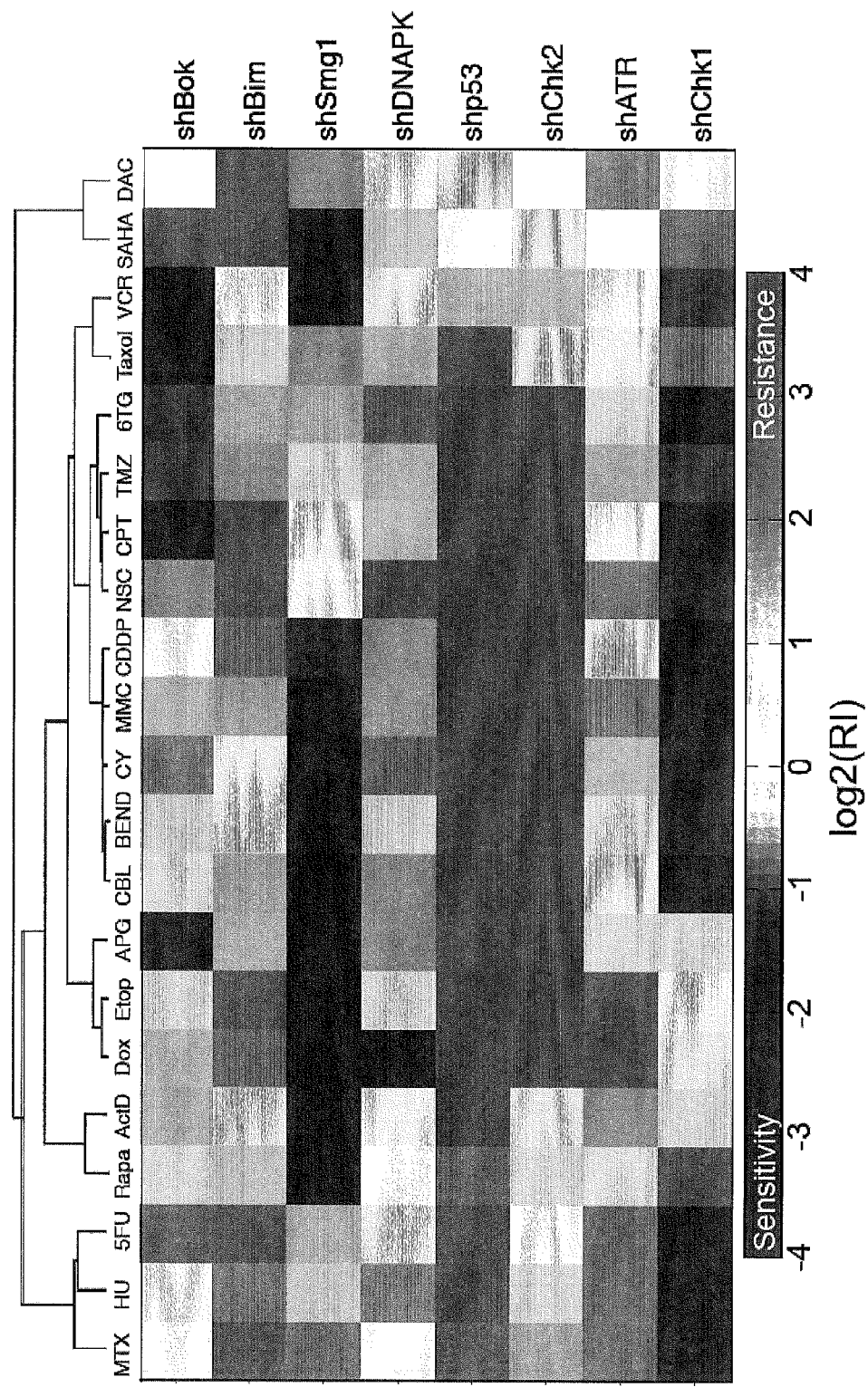

Given that a three-gene signature could effectively predict and classify genotoxic drugs, it was hypothesized that the combined resistance and sensitivity pattern of a small number of genes may be sufficient to accurately characterize most of our chemotherapeutic drugs in this cell line. To test this hypothesis, the seven drug clusters demarcated in our secondary analysis was examined (FIG. 1c) and it was asked which smaller sets of shRNAs could similarly define these groupings. Here, a K-nearest-neighbors cross-validation-based approach and a randomized search through 50,000 potential gene subsets was used. Although most smaller shRNA sets showed a significant loss in resolution relative to the reference set, it was found that a set of eight shRNAs, targeting p53, ATR, Chk1, Chk2, Smg-1, DNAPKcs, Bok and Bim, was able to classify the reference dataset with 100% accuracy and was highly correlated ($r^2=0.81$) with the original 29 shRNA signature (FIG. 4a and FIG. 11a, 11b). Although several other sets of eight shRNAs could also classify chemotherapeutics with 100% accuracy, this eight-shRNA signature had the highest range of measurement across all drugs. Notably, this eight-shRNA signature could also correctly classify bendamustine, CY190602, apigenin and NSC3852-drugs that were not included in the feature reduction and cross-validation of the eight-shRNA signature (FIG. 11c).

Figure 4B:
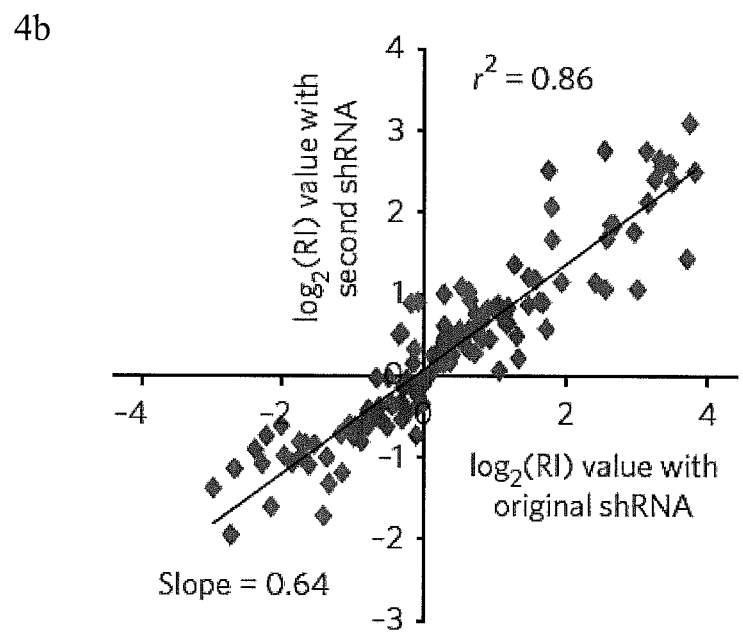
Figure 4C:
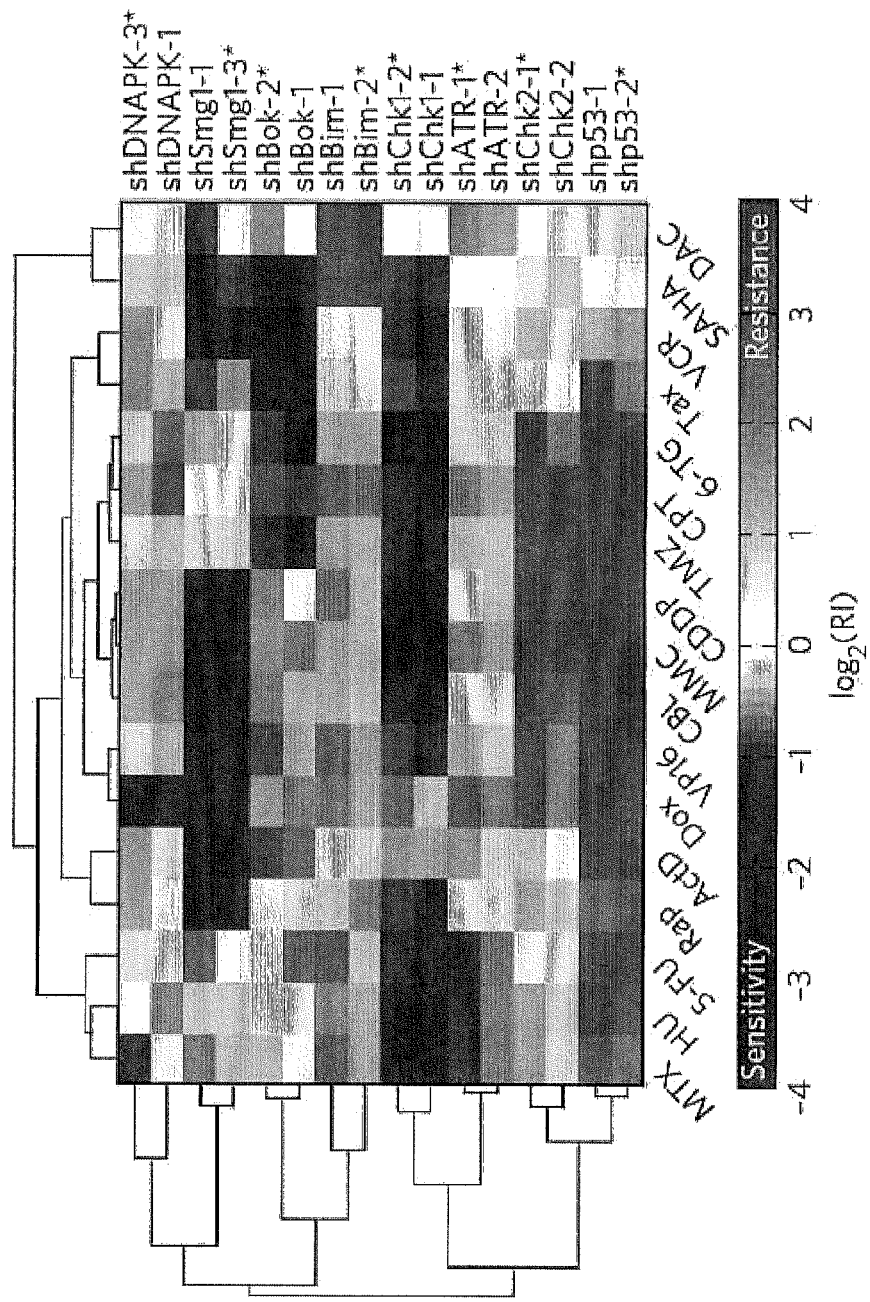

Given the known off-target potential of RNAi, it was next determined whether the functional signature derived from these eight shRNAs was attributable to the specific effect of shRNA target gene suppression on therapeutic response. To do this, a second set of shRNAs targeting the same eight genes was used to generate an independent drug response signature. Comparison of shRNA pairs revealed a high correlation between drug response signatures ($r^2=0.86$) in cells transduced with distinct shRNAs targeting the same gene; indicating that the major effects of these shRNAs are 'on target' (FIG. 4b). Additionally, unsupervised hierarchical clustering of the first eight-shRNA response signature or the combined response signatures generated using the first and second eight-shRNA sets revealed the same seven drug classes identified with the original 29-shRNA signature (FIG. 4c). Notably, however, the second set of eight shRNAs could independently predict only five out of seven drug classes. This loss of resolution in the second shRNA set may represent trace 'off-target' shRNA activity in either eight shRNA set. Alternatively, these differences may be attributable to small differences in the degree of target gene knockdown conferred by distinct hairpins. Consistent with the latter argument, shRNAs in the second set frequently showed reduced target gene suppression (FIGS. 7a-7b and Table 2) and yielded more subtle biological effects, as evidenced by the relative RI values seen in shRNA pairwise comparisons (FIG. 4b).

Figure 5A:
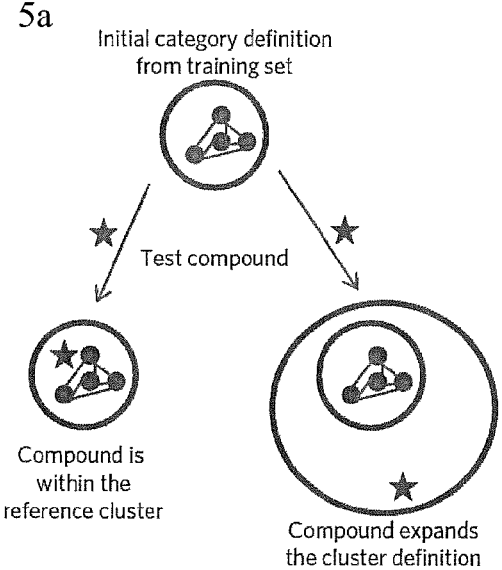
FIGS. 5a-5c: A reduced shRNA signature can accurately predict drug mechanism of action. (5a) A diagram of the possible outcomes for a test compound when it is compared to the training set. A test compound could be interpolated within the definition of a drug category that is provided by the training set (left). Alternatively, a test compound could be outside of the drug category (right). Our probabilistic nearest-neighbors algorithm attempts to define an "acceptable" category extension. (5b) A schematic depicting the methodology behind probabilistic nearest-neighbors predictions. An initial training set with empirically validated drug categories is used to calculate the drug category-specific cluster sizes. This same methodology is used for compounds whose known mechanism of action is distinct from a particular drug category. (5c) The increase in the drug category definition that is observed by forcing these empirically derived negative controls to cluster in an erroneous category is used to build a null distribution and an empirical cumulative distribution function.
Figure 5B:
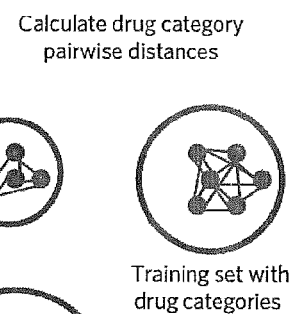
Figure 5C:
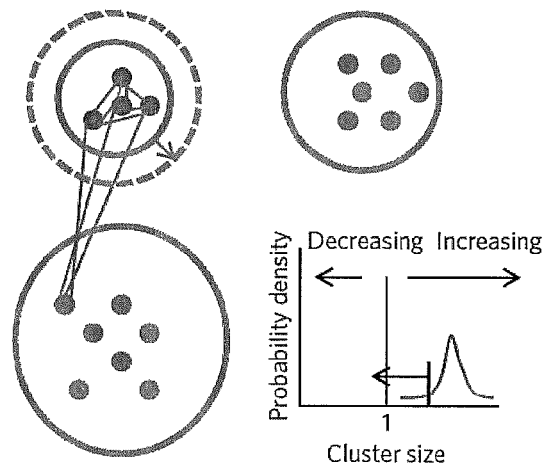

To extend the eight-shRNA signature approach in a scalable and stringent manner, a common problem in machine learning was revisited. A nonparametric classification method like K-nearest neighbors will classify any test compound according to its closest neighbor(s), even if the two compounds are quite distinct. Thus, it becomes difficult to determine how distantly a given compound can reside from a reference category of drugs and still be considered to share a similar mechanism of action (FIG. 5a). To overcome this problem, the carefully selected mechanistic diversity of the training set was taken advantage of to create specific empirical cumulative distribution functions for each drug category (FIG. 5b). This allowed the determination of whether a test compound was likely to belong to either an existing or a new drug category-a process critical to the broader applicability of this approach.

Figure 12:
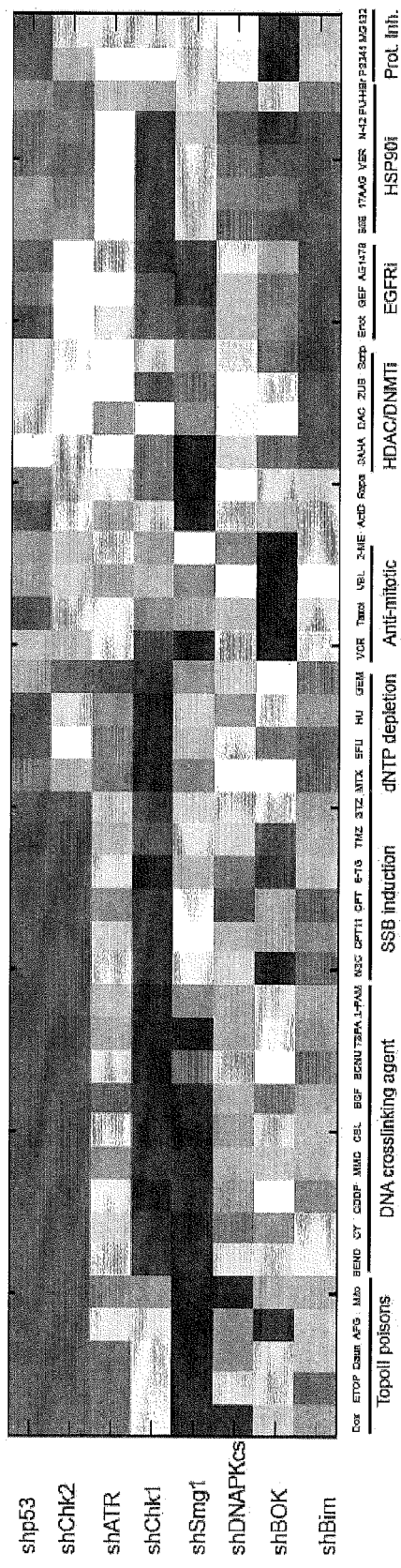
FIG. 12: A heat map showing the 8 shRNA resistance and sensitivity patterns of all chemotherapeutics examined.
Figure 13:
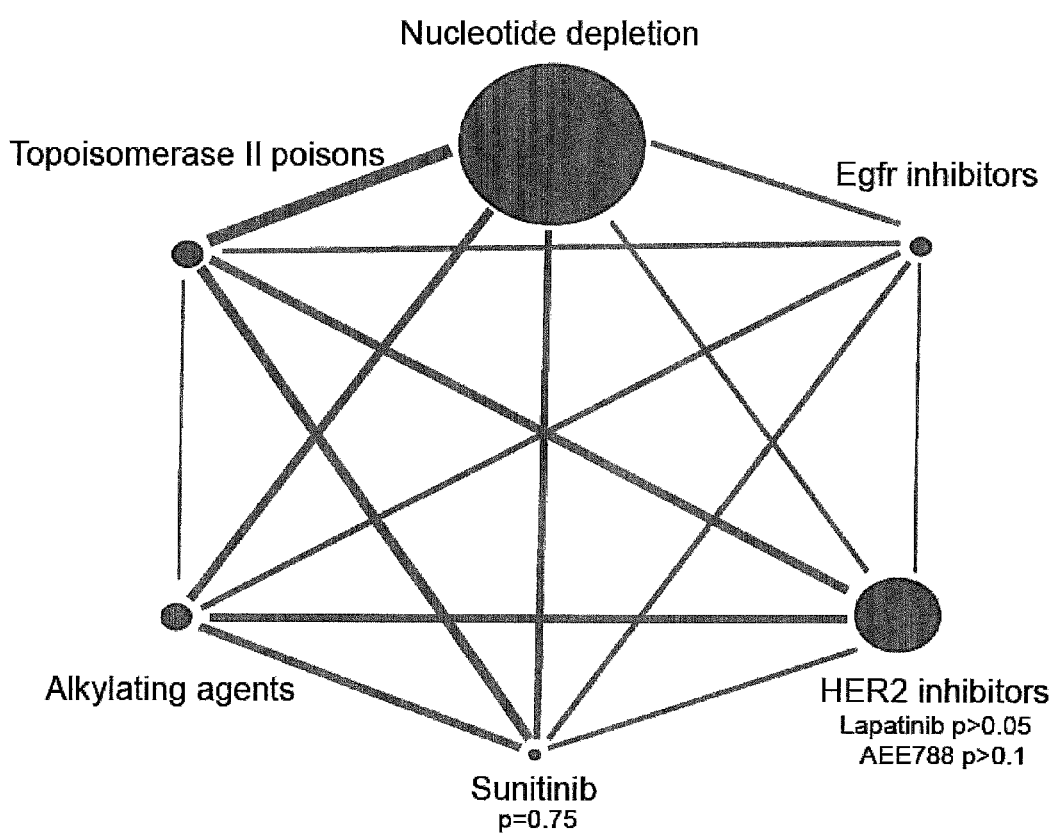
FIG. 13: A diagram showing the relative correlation distances within and between clusters. The bubble size represents the intracategory average linkage distance between drugs. The line thickness represents the average intercategory distances between the drugs of distinct categories. P values show how significantly HER2 inhibitors and Sunitib cluster with EGFR inhibitors.
Figure 14:
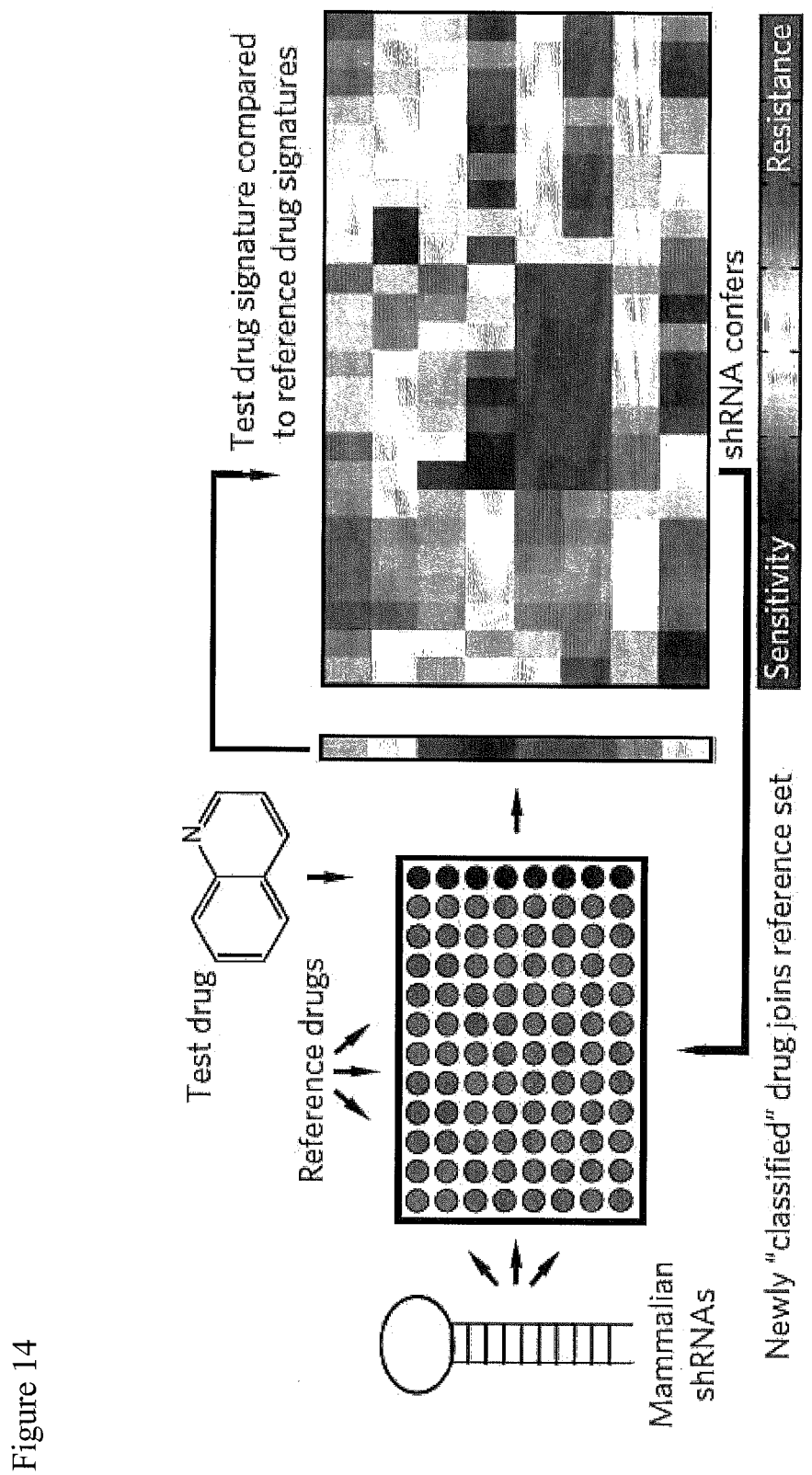
FIG. 14: Identifying the cellular targets of small molecules remains a central challenge of chemical biology. The application of an RNAi-based functional genomics approach permitted the clustering of drugs with related targets by "shRNA signatures" which served as a basis set to assign models of action to compounds with unknown targets.

To determine whether this methodology could correctly categorize chemotherapeutics absent from the initial reference set, a set of 16 additional anticancer drugs were examined (Table 1 and FIG. 12). In each case, the eight-shRNA approach successfully grouped drugs according to their mechanism of action. Importantly, when compounds that represent new drug categories were examined, they were not misclassified into the 'nearest' drug' category. Rather, they were identifiable as distinct agents that were significantly different from all other drug categories. Consequently although this eight-shRNA panel was assembled on the basis of responses to seven drug classes, it was also successful in predicting other classes of chemotherapeutics when the training set was updated with new reference compounds. For example, the eight shRNA signature accurately predicted that the proteasome inhibitor gliotoxin belonged to a drug category not represented by any of the existing reference drugs. However, when the proteasome inhibitors bortezomib (PS341) and MG132 were used to update the training set, the eight-shRNA signature was able to successfully classify gliotoxin and epoxomycin as proteasome inhibitors (Table 1). The eight-shRNA set could be similarly trained to identify two entirely distinct drug categories-Hsp90 inhibitors and EGFR inhibitors, neither of which was used to create the eight-shRNA reference set. Notably, the eight-shRNA signature could also distinguish functional drug subclasses within larger targeted classes of therapeutics. For example, the HER2 inhibitors lapatinib and AEE788 and the multikinase inhibitor sunitinib clustered in distinct categories relative to EGFR inhibitors (FIG. 13), despite all of these drugs belonging to the broader category of tyrosine kinase inhibitors. Although the use of more optimized sets of shRNAs may be necessary to probe fine details of certain drug categories, these data indicate that this eight-shRNA set has resolution over a broad range of cytotoxic activities.

Figure 6:
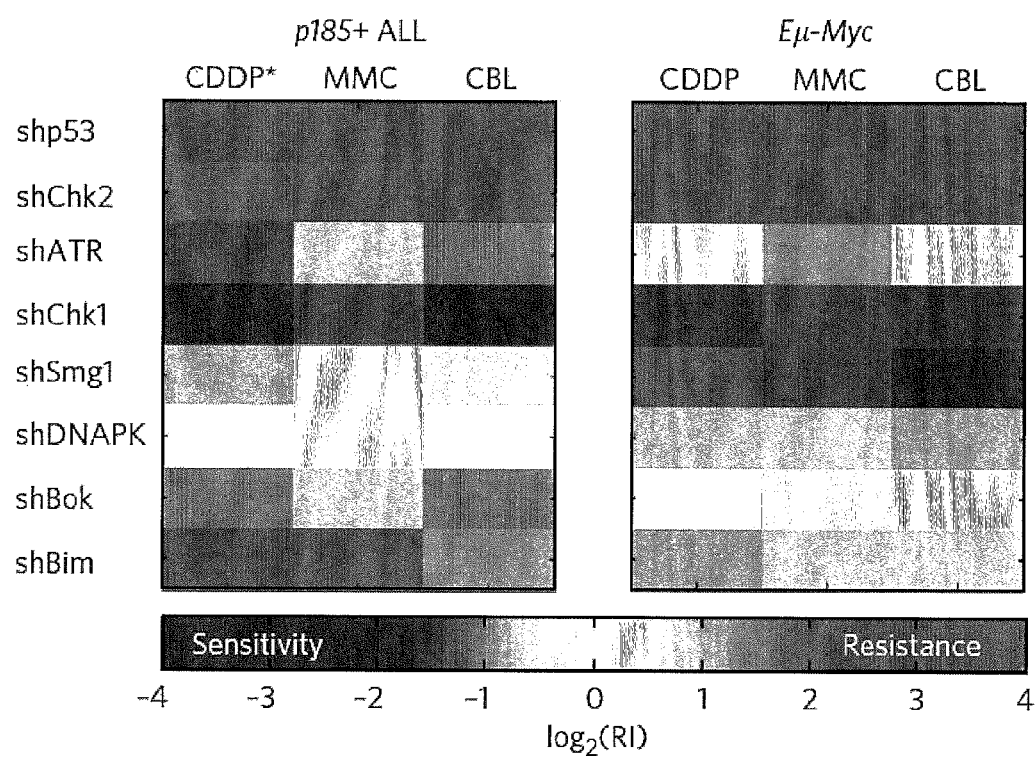
FIG. 6: Adaptation of the eight-shRNA signature to a distinct cell line. A heat map comparing the eight-shRNA response signatures of Myc p19$^{Afr-/-}$ lymphoma cells and p185+ BCR-Abl leukemia cells following treatment with alkylating agents in a model of acute lymphoblastic leukemia. The eight-shRNA signature from p185+ BCR-Abl p19$^{Afr-/-}$ leukemia cells can identify CDDP as an alkylating agent when CBL and MMC are used as a reference set.

Although the cells used in this study are responsive to a number of targeted chemotherapeutics, such as EGFR inhibitors, a potential limitation of this approach is that it lacks resolution for certain compounds requiring cellular targets not present in lymphoma cells. To determine whether this approach could be adapted to cell lines expressing targetable genetic lesions, the performance of the eight-shRNA signature in cells derived from a BCR-Abl-driven model of acute B cell leukemia (B-ALL) was examined (Williams, R T., et al., Proc. Natl. Acad, Sci. USA 103, 6688-6693 (2006)). Strikingly, a robust functional signature for alkylating agents could be generated in these cells using the same eight-shRNA set (FIG. 6). Notably, however, the response signature in B-ALL cells differed from that in lymphoma cells. For example, leukemia cells showed distinct genetic dependencies on ATR, DNA-PKcs and Bok. Thus, informative signatures can be derived in distinct cell lines, even if the signatures differ between cell types. Notably, this eight-shRNA signature may not be optimal for B-ALL cells, as feature reduction from the 29-shRNA signature was not performed in this context. Additionally, this signature may not have the same resolution as in lymphoma cells. However, these data indicate that even suboptimal signatures may provide resolution sufficient to cluster classes of chemotherapeutics.

Discussion

The functional genetic approach described herein has similarities to well-characterized chemogenomic profiling strategies in lower organisms. However, this approach also has notable advantages over existing genetic approaches for examining drug mechanisms of action and identifying drug targets. First, this approach is sufficiently sensitive to differentiate drugs with distinct targets but common downstream signaling pathways. For example, TopoI and II poisons produce distinct shRNA sensitivity profiles, yet both ultimately engage common transcriptional networks. Microarray approaches that focus on downstream changes in gene expression are, consequently, less able to distinguish between conventional anticancer agents. In fact, previous microarray studies have shown limited resolution over a number of frontline chemotherapeutics (Table 4). Second, this approach is unaffected by pharmacodynamic variability, such as distinctions in drug efflux or detoxification, that obscures comparisons between different cancer cell lines. Finally, and most importantly, this approach is both simple and tractable. Although microarray studies suffer from significant variability between experiments and laboratories, RNAi-based functional arrays are highly reproducible and can be widely disseminated.

Perhaps the most unanticipated aspect of this work lies in the quantity of information that can be derived from of a small set of mammalian loss-of-function phenotypes. This focused shRNA signature can characterize a diverse range of drug categories at high resolution and is extendable to completely new drug categories and distinct cell types, indicating that such signatures serve as a tractable approach to screen chemical libraries for diverse functional classes of small molecules in a high-throughput manner. Although this specific set of shRNAs may not provide optimal resolution for all cell types or small molecules, these data also indicate that alternative small sets of shRNAs may yield similar information content. For example, although this work focuses on cell viability, it is likely that given appropriate phenotypic resolution-bioactive compounds affecting diverse aspects of biology can similarly be interrogated with distinct targeted sets of shRNAs.

TABLE 1

| Compounds | Prediction | Linkage Ratio | P-value | Correct Prediction |
|---|---|---|---|---|
| Daunorubicin | TopoII poison | 0.83 | 0.0004 | Yes |
| Zebularine | HDAC/DNMT inhibitor | 0.82 | 0.002 | Yes |
| Busulfan | DNA cross-linking | 0.97 | 0.007 | Yes |
| 2-Methoxyestradiol | Antimicrotubule | 1.08 | 0.009 | Yes |
| Vinblastine | Antimicrotubule | 0.95 | 0.001 | Yes |
| Scriptaid | HDAC/DNMT inhibitor | 0.85 | 0.004 | Yes |
| Carmustine | DNA cross-linking | 0.95 | 0.005 | Yes |
| Mitoxantrone | TopoII poison | 0.94 | 0.002 | Yes |
| Thiotepa | DNA cross-linking | 0.92 | 0.003 | Yes |
| Gemcitabine | Nucleotide synthesis inhibitor | 0.93 | 0.002 | Yes |
| Melphanlan | DNA cross-linking | 0.91 | 0.002 | Yes |
| Carboplatin | DNA cross-linking | 0.86 | 0.0008 | Yes |
| Streptozocin | SSB inducer | 1.03 | 0.02 | Yes |
| Mephosphamide | DNA cross-linking | 0.93 | 0.003 | Yes |
| Irinotecan | SSB inducer | 0.88 | 0.002 | Yes |
| Noscapine | Antimicrotubule | 0.83 | 0.0002 | Yes |
| Cantharidin | Novel mechanism | 1.27 | 0.10 | Negative control |
| AA2 | Novel mechanism | 1.39 | 0.30 | Negative control |
| Gliotoxin | Novel mechanism | 1.11 | 0.09 | Negative control |
| AG1478 | Novel mechanism | 1.08 | 0.06 | Negative control |

(a) Table showing the predictive power of the eight-shRNA signature on a set of drugs that were not used to derive the signature. The Prediction column indicates the mechanism of action of the compound as predicted by a nearest-neighbors approach. The linkage ratio describes the proximity of a test compound to a particular class of compounds and defines the observed increase (or decrease) in drug category site. For example, a linkage ratio of 1:1 indicates that the addition of a new drug expands the drug category by 10%. The p-value describes whether the proximity of a compound to a given drug category is significant when compared to a negative control distribution for that drug category. Cantharidin (a protein phosphatase inhibtor), apoptosis activator 2 (AA2, a direct activator of the apoptosome), gliotoxin (a proteasome inhibitor) and AG1478 (an EGFR inhibitor) were used as negative controls and were predicted to be distinct from any of the existing reference drugs.

(b) Category predictions and signifcance levels upon adding three new drug categories (proteasome, Hsp90 and EGFR inhibitors) that were not used to delvelop the intial eight-shRNA signature. PU-H71-Br is a chemical derivative of the benzyladenine-based Hsp90 inhibitor PU-H71. VER-50589 and neopentylamine-42 are hsp90 inhibitors. PD 173074 (a FGFR inhibitor) and GDC 0940 (a PI3K Inhinbitor) were used as negative controls to test the stringency of predictions after the incorporaation of these new drug categories.

TABLE 2 shRNA Target Sequences

| Gene | Gene Function | Gene ID | shRNA Target Sequences* |
|---|---|---|---|
| p53 | sequence-specific transcription factor, pro-apoptotic | 22059 | CCACTACAAGTACATGTGTAA (SEQ ID NO: 1) TGGAGAGTATTTCACCCTCAA (18%) (SEQ ID NO: 2) |
| ATM | DNA damage response, checkpoint signaling, DNA repair, phosphorylation of p53 DNA damage response, checkpoint signaling, | 11920 | CACGAAGTCCTCAATAATCTA (SEQ ID NO: 3) CAGAAACACATAATCATTAAA (SEQ ID NO: 4) |
| Chk2 | DNA repair, phosphorylation of p53 DNA repair, DNA replication, phosphorylation of | 50883 | CACTTTCACTATGTAGAAATA (SEQ ID NO: 5) ACCCATGTTCTTGACATTGAA (SEQ ID NO: 6) |

TABLE 2-continued shRNA Target Sequences

| Gene | Gene Function | Gene ID | shRNA Target Sequences* |
|---|---|---|---|
| ATR | p53<br>DNA repair, DNA replication, phosphorylation of | 245000 | ACCTTTAATGAGTGTCTTAAA (SEQ ID NO: 7)<br>CAGGAATATTCTGATTGGAAA (SEQ ID NO: 8) |
| Chk1 | p53 | 12649 | AAGGGCTTGACCAATTATAAA (SEQ ID NO: 9) |
| Smg1 | nonsense-mediated mRNA decay, DNA damage response, checkpoint signaling, phosphorylation of p53 | 233789 | CAGGATAGCAATAAAGATGAA<br>CAGGCTGCATTCAATAACTTA (SEQ ID NO: 10) |
| DNA-PKcs | DNA damage response, DNA repair phosphorylation of p53 | 19090 | CAGGCCTATACTTACAGTTAA<br>CTCCAACATGTAGAGAACAAA (SEQ ID NO: 11) |
| JNK1 | DNA damage response, stress signaling, phosphorylation of p53 | 26419 | TCAGAGCATAACAAACTTAAA (SEQ ID NO: 12) |
| p38 | DNA damage response, checkpoint signaling, stress signaling, phosphorylation of p53 | 26416 | CAGGTCTTGTGTTTAGGTCAA (SEQ ID NO: 3) |
| A1 | Bcl-2 family gene, anti-apoptotic | 12044 | GGAAGATGGCTTCATAAAGAA (SEQ ID NO: 14) |
| Bclb | Bcl-2 family gene, anti-apoptotic | 12049 | AAGGAATCCCTTGAAACCTAA (SEQ ID NO: 15) |
| Bclw | Bcl-2 family gene, anti-apoptotic | 12050 | GGCTATAAGCTGAGGCAGAAG (SEQ ID NO: 16) |
| Bclx | Bcl-2 familpro-y gene, anti-apoptotic (long form), apoptotic (short form) | 12048 | GGAGAGCGTTCAGTGATCTAA (SEQ ID NO: 17) (targets both long and short forms of Bclx) |
| Bad | BcI-2 family gene, pro-apoptotic | 12015 | CGCGAGAAACGTGCTTTATAA (SEQ ID NO: 18) |
| Bak | Bcl-2 family gene, pro-apoptotic | 12018 | CCGGAACCTATGATTACTTGA (SEQ ID NO: 19) |
| Bax | Bcl-2 family gene, pro-apoptotic | 12028 | CCGCGTGGTTGCCCTCTTCTA (SEQ ID NO: 20) |
| Bid | Bcl-2 family gene, pro-apoptotic | 12122 | CACAGAAGATTCCATATCAAA (SEQ ID NO: 21) |
| Bik | Bcl-2 family gene, pro-apoptotic | 12124 | CCGGACAGGTGTCAGAGGTAT (SEQ ID NO: 22)<br>TAGGAACAGAGAAATATGCAA (SEQ ID NO: 23) |
| Bim | BcI-2 family gene, pro-apoptotic | 12125 | CACCCTCAAATGGTTATCTTA (22%) (SEQ ID NO: 24) |
| Bmf | BcI-2 family gene, pro-apoptotic | 171543 | CGCAGAGCCCTGGCATCACAA (SEQ ID NO: 25) |
| Bnip3I | Bcl-2 family gene, pro-apoptotic | 12177 | GGTATCAGACTGGTCCAGTAG (SEQ ID NO: 26) |
| Bclg | Bcl-2 family gene, less defined | 66813 | TCCAAACAGCATAGAGTTCAA (SEQ ID NO: 27)<br>CTGGCCTCTGTGACTGCTCTA (SEQ ID NO: 28) |
| Bok | Bcl-2 family gene, less defined | 51800 | TCGGTGTCCAGCCCTAGAGAA (25%) (SEQ ID NO: 29) |
| BPR | Bcl-2 family gene, less defined | 75736 | CCCAGCCTCTTCCGAGTTCTA (SEQ ID NO: 30) |

TABLE 2-continued shRNA Target Sequences

| Gene | Gene Function | Gene ID | shRNA Target Sequences* |
|------|---------------|---------|-------------------------|
| Hrk | Bcl-2 family gene, pro-apoptotic | 12123 | CAGCAGGGAGTGTCTACTTTA (SEQ ID NO: 31) |
| Mil1 | Bcl-2 family gene, pro-apoptotic | 94044 | CCTGAAGAAGTGAAGAGCTTA (SEQ ID NO: 32) |
| Mule | Bcl-2 family gene, E3 ligase for Mcl-1 and p53 | 59026 | CCACCTCAGCTACTTCAAGTT (SEQ ID NO: 33) |
| Noxa | Bcl-2 family gene, pro-apoptotic | 58801 | CAGATTGAATAGTATGTGATA (SEQ ID NO: 34) |
| Puma | Bcl-2 family gene, pro-apoptotic | 170770 | CTGTAGATATACTGGAATGAA (SEQ ID NO: 35) |

TABLE 3

| Drug Name | Abbreviation | Mechanism of Action | Drug Category | Concentration used* |
|-----------|--------------|---------------------|---------------|---------------------|
| Chlorambucil | CBL | DNA crosslinking | Alkylating agent | 6.6 uM |
| Bendamustine | | DNA crosslinking | Alkylating agent | 110 uM |
| CY-190602 | CY-B | DNA crosslinking | Alkylating agent | 1.4 uM |
| Melphalan | L-PAM | DNA crosslinking | Alkylating agent | 3.9 uM |
| Maphosphamide | MAF | DNA crosslinking | Alkylating agent | 6.9 uM |
| Carmustine | BCNU | DNA crosslinking | Alkylating agent | 26.7 uM |
| Busulfan | BSF | DNA crosslinking | Alkylating agent | 40.6 uM |
| ThioTEPA | TSPA | DNA crosslinking | Alkylating agent | 2.1 uM |
| Carboplatin | CDDPC | DNA crosslinking | Platinum | 16.4 uM |
| Cisplatin | CDDP | DNA crosslinking | Platinum | 3.3 uM |
| Mitomycin C | MMC | DNA crosslinking | Anti-tumor antibiotic | 90 nM |
| Camptothecin | CPT | Induction of SSBs | Topo I poison | 0.4 nM |
| Irinotecan | CPT11 | Induction of SSBs | Topo I poison | 2.1 uM |
| NSC3852 | NSC3852 | Induction of SSBs | Topo I poison | 1.7 uM |
| Doxorubicin | Dox | Induction of DSBs | Topo II poison | 16.2 nM |
| Etoposide | VP16 | Induction of DSBs | Topo II poison | 34 nM |
| Mitoxantrone | MITO | Induction of DSBs | Topo II poison | 0.4 nM |
| Apigenin | APG | Induction of DSBs | Topo II poison | 100 nM |
| Daunorubicin | Dau | Induction of DSBs | Topo II poison | 22.5 nM |
| 6-Thioguanine | 6TG | DNA methylation memetic | Antimetabolite | 54 nM |
| Temozolomide | TMZ | DNA methylation | Alkylating agent | 23.2 uM |
| Streptozocin | STZ | DNA methylation | Alkylating agent | 83 uM |
| 17 AAG | | HSP90 inhibition | HSP90 inhibitor | 2.6 uM |
| BIIB021 | | HSP90 inhibition | HSP90 inhibitor | 0.79 uM |
| PU-H71-Br | | HSP90 inhibition | HSP90 inhibitor | 0.53 uM |
| Neopentylamine 42 | | HSP90 inhibition | HSP90 inhibitor | 1.1 uM |
| VER-50589 | | HSP90 inhibition | HSP90 inhibitor | 0.16 uM |
| Vorinostat | SAHA | HDAC inhibition | HDAC inhibitor | 0.2 uM |
| Scriptaid | | HDAC inhibition | HDAC inhibitor | 0.5 uM |
| Decitabine | DAC | DNMT inhibition | Antimetabolite | 0.6 uM |
| Zebularine | | DNMT inhibition | Antimetabolite | 30 uM |
| PD 173074 | | FGFR inhibition | FGFR inhibitor | 4.2 uM |
| AG1478 | | EGFR inhibition | EGFR inhibitor | 19 uM |
| Gefitinib | | EGFR inhibition | EGFR inhibitor | 12.5 uM |
| Erlotinib | | EGFR inhibition | EGFR inhibitor | 6.5 uM |
| GDC 0941 | | PI3K inhibition | PI3K inhibitor | 5.4 uM |
| Actinomycin D | ActD | RNA syn. inhibition | Anti-tumor antibiotic | 1.2 nM |
| Roscovitine | Rosco | CDK inhibition | Kinase inhibitor | 26.7 uM |
| Rapamycin | RAPA | Protein syn. inhibition | Anti-tumor antibiotic | 15 uM |
| Bortezomib | PS341 | Proteasome inhibition | Proteasome inhibitor | 13 nM |
| Epoxomicin | | Proteasome inhibition | Proteasome inhibitor | 45 nM |
| Gliotoxin | | Proteasome inhibition | Proteasome inhibitor | 0.3 uM |
| Vinblastine | VLB | Disruption of mitosis | Antimicrotuble agent | 2.5 nM |
| Paclitaxel | Taxol | Disruption of mitosis | Antimicrotuble agent | 8 nM |
| Vincristine | VCR | Disruption of mitosis | Antimicrotuble agent | 1.5 nM |
| Noscapine | | Disruption of mitosis | Antimicrotuble agent | 58.1 uM |
| 2-Methoxyestradiol | | Disruption of mitosis | Antimicrotuble agent | 1.8 uM |
| Methotrexate | MTX | nucleic acid syn. inhibition | Antimetabolite | 33 nM |
| 5-Fluorouracil | 5FU | nucleic acid syn. inhibition | Antimetabolite | 30.5 uM |
| Hydroxyurea | HU | nucleic acid syn. inhibition | Antimetabolite | 78 uM |
| Fludarabine | dFdC | nucleic acid syn. inhibition | Antimetabolite | 3.8 uM |
| Gemcitabine | GEM | nucleic acid syn. inhibition | Antimetabolite | 100 nM |

TABLE 3-continued

| Drug Name | Abbreviation | Mechanism of Action | Drug Category | Concentration used* |
|---|---|---|---|---|
| Cantharidin | | Phophatase inhibition | Phophatase inhibitor | 10.7 uM |
| Apoptosis Activator 2 | AA2 | Direct activation of apoptosome | Activator of apoptosis | 1.9 uM |

TABLE 4

| Rank | cmap name | Mean | n | Enrichment | p | Specificity | Percent non-null | Known Mechanism/Target |
|---|---|---|---|---|---|---|---|---|
| a |
| Vorinostat query |
| 1 | vorinostat | 0.743 | 12 | 0.976 | 0 | 0.0151 | 100 | HDACl |
| 2 | trichostatin A | 0.631 | 182 | 0.898 | 0 | 0.095 | 97 | HDACl |
| 3 | resveratrol | 0.275 | 9 | 0.757 | 0 | 0.0343 | 100 | HDACl |
| 4 | 15-delta prostagland | 0.16 | 15 | 0.589 | 0 | 0.11763 | 86 | PPAR-gamma agonist |
| 5 | thioridazine | 0.169 | 20 | 0.588 | 0 | 0.1324 | 75 | Seratonin antagonist |
| 6 | geldanamycin | 0.203 | 15 | 0.587 | 0 | 0.0924 | 86 | HSP90i |
| 7 | LY-294002 | 0.202 | 61 | 0.578 | 0 | 0.0134 | 85 | PI3KI |
| 8 | sirollmus | 0.143 | 44 | 0.515 | 0 | 0.0361 | 68 | mTOR |
| 9 | valproic acid | 0.206 | 57 | 0.512 | 0 | 0 | 70 | HDACl |
| 10 | tanespimycin | 0.172 | 62 | 0.503 | 0 | 0.0725 | 80 | HSP90i |
| Geldanamycin query |
| 1 | withafarin A | 0.345 | 4 | 0.969 | 0 | 0.0211 | 100 | Heat shock response inducer |
| 2 | lomustine | 0.311 | 4 | 0.941 | 0 | 0.0118 | 100 | Alkylating agent |
| 3 | geldanamycin | 0.522 | 15 | 0.925 | 0 | 0 | 100 | HSP90i |
| 4 | tanespimycin | 0.438 | 62 | 0.827 | 0 | 0.0052 | 98 | HSP90i |
| 5 | alvespimycin | 0.394 | 12 | 0.802 | 0 | 0.0058 | 100 | HSP90i |
| 8 | vorinostat | 0.263 | 12 | 0.742 | 0 | 0.1759 | 91 | HDACl |
| 7 | monorden | 0.302 | 22 | 0.719 | 0 | 0.0054 | 100 | Poorly characterized in mammals |
| 8 | 15-delta prostagland | 0.282 | 15 | 0.71 | 0 | 0.0335 | 93 | PPAR-gamma agonist |
| 9 | trifluoperazine | 0.177 | 16 | 0.631 | 0 | 0.0529 | 68 | Dopamine D1, D2 receptor |
| 10 | thioridazine | 0.123 | 20 | 0.599 | 0 | 0.1279 | 50 | Anti-cholinergic |
| b |
| Chlorambucil query |
| 1 | monensin | −0.337 | 6 | −0.831 | 0.00006 | 0 | 50 | Ionophore |
| 2 | nialamide | 0.223 | 4 | 0.909 | 0.00008 | 0 | 100 | MAOI |
| 3 | quinethazone | 0.206 | 4 | 0.877 | 0.00034 | 0 | 100 | Anti-hypertensive |
| 4 | capsaicin | 0.161 | 4 | 0.86 | 0.0005 | 0 | 100 | VR1 agonist |
| 5 | fluocinonide | 0.14 | 5 | 0.774 | 0.00134 | 0.0075 | 80 | Glucocorticoid |
| 6 | Prestwick-983 | −0.732 | 3 | −0.905 | 0.00162 | 0.0069 | 100 | Poorly characterized |
| 7 | biperiden | −0.56 | 5 | −0.751 | 0.00174 | 0.0748 | 80 | Anti-cholinergic |
| 8 | bendroflumethiazide | 0.157 | 6 | 0.75 | 0.00175 | 0 | 83 | Anti-hypertensive |
| 9 | cefamandole | −0.345 | 4 | −0.805 | 0.00282 | 0.0083 | 50 | Beta-lactam antibiotic |
| 10 | lkarugamycin | −0.467 | 3 | −0.885 | 0.00296 | 0.0152 | 66 | Eridocytosis inhibitor |
| 90 | semustine | 0.103 | 4 | 0.568 | 0.09445 | 0.3051 | 75 | Alkylating agent |
| Vinblastine query |
| 1 | methotrexate | −0.473 | 8 | −0.679 | 0.00044 | 0.0069 | 87 | Nucleotide depletion |
| 2 | niledipine | 0.061 | 7 | 0.696 | 0.00056 | 0 | 71 | Calcium channels |
| 3 | doxylamine | −0.273 | 5 | −0.796 | 0.00074 | 0.0267 | 60 | Anti-histamine |
| 4 | Prestwick-642 | 0.148 | 4 | 0.844 | 0.00097 | 0 | 100 | Poorly characterized |
| 5 | meptazinol | −0.635 | 4 | −0.828 | 0.00165 | 0.0054 | 100 | Opioid receptor agonist |
| 6 | pirenperone | 0.089 | 5 | 0.758 | 0.00194 | 0 | 60 | 5-HT2A receptor |
| 7 | valinomycin | 0.119 | 4 | 0.811 | 0.00241 | 0.0349 | 100 | K+ Carrier |
| 8 | cinnarizine | 0.12 | 4 | 0.805 | 0.00269 | 0 | 100 | Anti-histamine |
| 9 | (−)-atenolol | 0.12 | 4 | 0.8 | 0.00302 | 0 | 100 | Beta blocker |
| 10 | urapidil | 0.114 | 4 | 0.796 | 0.0032 | 0 | 100 | Alpha-1 adrenergic receptor |
| 271 | podophyllotoxin | 0.079 | 4 | 0.434 | 0.32889 | 0.7286 | 50 | Microtubule assembly |

| c | |
|---|---|
| Connectivity Map Comparison Criteria | Out of 14 |
| Top hit is either a replicate of the same compound or a compound with the same mechanism | 6 |
| At least one of the top 5 is the same mechanism | 10 |
| At least one of the top 10 is the same mechanism | 10 |

A summary of small molecule queries using the Connectivity Map. a, Tables showing results in which compounds—Vorinostat (above), and Geldanamycin (below) were queried against the connectivity map. These compounds show clear mechanistic signatures characteristic of their molecular drug class. Analogous compounds present in the top 10 search results are shown in red. b, Tables showing results in which the queried compounds are vinblastine and chlorambucil. The red text indicates the first compound with a known mechanistic relationship. Notably, while the 8-shRNA can effectively classify these compounds, the Connectivity Map lacks resolution for either agent. All data was obtained at: www.broadinstitute.org/cmap/.c, Connectivity Map analysis of 14 compounds categorized in this study. The drugs examined were Mitoxantrone, Doxorubicin, Daunorubicin, Camptothecin, Irinotecan, Carmustine, Vinblastine, Paclitaxel, Methotrexate, Vorinostat, Geldanamycin, Lomustine, MG132, and Rapamycin.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method of characterizing a mechanism of action of an agent comprising:
    a) contacting each of eight populations of cells with an agent to be assessed, wherein each population of cells expresses a small hairpin RNA (shRNA) that targets one of eight genes present in the cells, said eight genes consisting of p53, ATR, Chk1, Chk2, Smg-1, DNA-PKcs, Bok, and Bim genes; and
    b) determining a responsiveness of each of the eight populations of cells to the agent to obtain a combined shRNA signature of the agent for the eight populations of cells,
thereby characterizing the mechanism of action of the agent.

2. The method of claim 1 wherein the mechanism of action of the agent comprises inhibition of a topoisomerase, cross linking of DNA, inducement of single stand break of DNA, inhibition of nucleic acid synthesis, inhibition of mitosis, inhibition of RNA transcription, inhibition of histone modification enzymes, inhibition of heat shock proteins, alkylation of DNA, or inhibition of proteasomes inducement of apoptosis.

3. The method of claim 1 further comprising classifying the agent within a group of agents having in common one or more mechanisms of action.

4. The method of claim 1 wherein each shRNA acts to knock down the gene that it targets.

5. The method of claim 1 wherein the agent is used in an effective amount to induce a response in cells that do not contain shRNA targeting any of said eight genes.

6. The method of claim 1 wherein the agent is a derivative of a chemotherapeutic agent.

7. The method of claim 1 wherein the responsiveness of each of the populations of cells to the agent is a relative level of chemo-resistance and sensitization conferred by each shRNA.

8. The method of claim 1 wherein the responsiveness of each of the populations of cells to the agent is a relative survival rate compared to control cells that do not contain shRNA targeting any of the eight genes.

9. The method of claim 1 wherein each of the populations of cells further expresses a marker gene.

10. The method of claim 1 wherein the shRNAs are introduced into the cells using a viral vector.

11. The method of claim 10 wherein the viral vector is a retroviral vector.

12. The method of claim 10 wherein the vector further expresses a marker gene.

13. The method of claim 9 wherein the marker gene is a fluorescent marker gene.

14. The method of claim 9 wherein the marker gene is green fluorescent protein (GFP) gene.

15. The method of claim 13 further comprising measuring the fluorescent marker gene or GFP gene expression level in each of the populations of cells using flow cytometry.

16. The method of claim 1 further comprising comparing the responsiveness of each of the populations of cells to the agent to a control.

17. The method of claim 16 wherein the control is a population of cells into which no shRNA targeting any of the eight genes has been introduced.

18. The method of claim 1 wherein the determination of the responsiveness is accomplished using cell flow cytometry, hybridization techniques or sequencing techniques.

19. The method of claim 1 wherein each of the populations of cells is contacted repeatedly with the agent.

20. The method of claim 1 further comprising introducing the shRNAs into each of the populations of cells.

21. The method of claim 1 further comprising, using a processor, clustering representations of a plurality of agents into groups based on the responsiveness of each of the populations of cells to each agent.

22. The method of claim 1 wherein the agent is a chemotherapeutic or genotoxic agent.

23. The method of claim 1 wherein the agent is a chemical compound.

24. The method of claim 1 further comprising assessing whether the agent has a chemotherapeutic or genotoxic effect.

25. The method of claim 21 wherein clustering the representations of the plurality of agents into groups includes:
    determining an initial cluster size of a group of agents by determining an average of pairwise linkage distances among the group of agents, the group of agents formed based on the responsiveness of each of the populations of cells to each agent of the group;
    predicting whether the agent belongs to the group using a k-nearest neighbor calculation between the agent and the group of agents; and
    if the agent is predicted to belong to the group, adding the agent to the group and determining a new cluster size for the group of agents, and determining a linkage ratio for the agent and the group of agents based on the initial cluster size and the new cluster size.

26. The method of claim 25 wherein a linkage ratio of less than one indicates that adding the agent to the group reduced an average distance between agents in the group, and a linkage ratio of greater than one indicates that adding the agent to the group increased an average distance between agents in the group.

27. The method of claim 25 wherein the k-nearest neighbor calculation includes cross-validating the group of agents by leaving out one of the agents from the group and predicting the left-out agent's identity based on the remaining agents in the group.

28. The method of claim 25 further comprising estimating a significance of adding the agent to the group by sampling negative control distributions of the group of agents.

29. The method of claim 25 further comprising determining distances between a plurality of groups using a centroid linkage.

30. The method of claim 29 further comprising estimating a significance of the groupings using a Monte Carlo analysis.

* * * * *

UNITED STATES PATENT AND TRADEMARK OFFICE
CERTIFICATE OF CORRECTION

PATENT NO. : 9,683,231 B2  
APPLICATION NO. : 13/993930  
DATED : June 20, 2017  
INVENTOR(S) : Hai Jiang et al.

Page 1 of 1

It is certified that error appears in the above-identified patent and that said Letters Patent is hereby corrected as shown below:

On the Title Page

In item (86), delete "Jan. 29, 2014" and insert -- Jan. 28, 2014 --.

Signed and Sealed this  
Fifteenth Day of August, 2017

Joseph Matal  
*Performing the Functions and Duties of the*  
*Under Secretary of Commerce for Intellectual Property and*  
*Director of the United States Patent and Trademark Office*